US010745413B2

(12) United States Patent
Davidson et al.

(10) Patent No.: US 10,745,413 B2
(45) Date of Patent: Aug. 18, 2020

(54) COMMERCIALLY VIABLE SYNTHESIS OF CANTHARIDIN AND BIOACTIVE CANTHARIDIN DERIVATIVES

(71) Applicant: Verrica Pharmaceuticals, Inc., San Carlos, CA (US)

(72) Inventors: Matthew Davidson, San Carlos, CA (US); Steven R. Schow, Redwood City, CA (US)

(73) Assignee: Verrica Pharmaceuticals, Inc., West Chester, PA (US)

( * ) Notice: Subject to any disclaimer, the term of this patent is extended or adjusted under 35 U.S.C. 154(b) by 84 days.

(21) Appl. No.: 15/535,860

(22) PCT Filed: Dec. 17, 2015

(86) PCT No.: PCT/US2015/066487
§ 371 (c)(1),
(2) Date: Jun. 14, 2017

(87) PCT Pub. No.: WO2016/100732
PCT Pub. Date: Jun. 23, 2016

(65) Prior Publication Data
US 2019/0002474 A1    Jan. 3, 2019

Related U.S. Application Data

(60) Provisional application No. 62/093,396, filed on Dec. 17, 2014.

(51) Int. Cl.
| C07D 493/18 | (2006.01) |
| C07D 497/18 | (2006.01) |
| C07D 497/04 | (2006.01) |
| C07D 333/38 | (2006.01) |
| A61K 31/381 | (2006.01) |

(52) U.S. Cl.
CPC .......... C07D 497/18 (2013.01); A61K 31/381 (2013.01); C07D 333/38 (2013.01); C07D 497/04 (2013.01)

(58) Field of Classification Search
CPC ... C07D 493/18; C07D 495/18; C07D 495/08
See application file for complete search history.

(56) References Cited

U.S. PATENT DOCUMENTS

| 4,148,874 A | 4/1979 | Smith |
| 4,298,752 A | 11/1981 | Dauben et al. |
| 4,895,727 A | 1/1990 | Allen |
| 5,445,462 A | 8/1995 | Johnson et al. |
| 5,590,780 A | 1/1997 | O'Meara |
| 5,702,694 A | 12/1997 | Chamness |
| 6,673,031 B2 | 1/2004 | Mark |
| 8,518,076 B2 | 8/2013 | Stenton |
| 8,871,801 B2 | 10/2014 | Levitt |
| 2003/0068331 A1 | 4/2003 | Battaglia et al. |
| 2003/0072814 A1 | 4/2003 | Maibach et al. |
| 2004/0242770 A1 | 12/2004 | Feldstein et al. |
| 2005/0019418 A1 | 1/2005 | Crutchfield et al. |
| 2005/0111900 A1 | 5/2005 | Fazzolari et al. |
| 2005/0169696 A1 | 8/2005 | Albisetti |
| 2006/0110415 A1 | 5/2006 | Gupta |
| 2007/0000566 A1 | 1/2007 | Gueret |
| 2007/0111954 A1 | 5/2007 | Crutchfield et al. |
| 2007/0187437 A1 | 8/2007 | Lord |
| 2008/0146674 A1 | 6/2008 | Rosenberg et al. |
| 2008/0195040 A1 | 8/2008 | Clark et al. |
| 2009/0311028 A1 | 12/2009 | Odermatt et al. |
| 2011/0208136 A1 | 8/2011 | Sollingen et al. |
| 2011/0212033 A1 | 9/2011 | Tamarkin et al. |
| 2012/0016320 A1 | 1/2012 | Lin |
| 2012/0148520 A1 | 6/2012 | Strobel et al. |
| 2012/0190658 A1 | 7/2012 | Studin |
| 2012/0312709 A1 | 12/2012 | Kaufman |
| 2013/0004230 A1 | 1/2013 | Kirk et al. |
| 2013/0197075 A1 | 8/2013 | Levitt |
| 2014/0275248 A1 | 9/2014 | Johnson |
| 2015/0118164 A1 | 4/2015 | Tamarkin et al. |
| 2016/0193177 A1 | 7/2016 | Davidson |
| 2017/0305925 A1 | 10/2017 | Piotrowski et al. |
| 2019/0031674 A1 | 1/2019 | Davidson et al. |

FOREIGN PATENT DOCUMENTS

| CN | 1966508 A | 5/2007 |
| CN | 101108853 B | 5/2010 |
| CN | 101036774 B | 12/2010 |
| CN | 102146086 A | 8/2011 |
| CN | 102268006 A | 12/2011 |
| CN | 202920809 | 5/2013 |
| EP | 0841059 A1 | 5/1998 |
| JP | 47-39621 | 11/1972 |
| JP | 05-058914 | 3/1993 |

(Continued)

OTHER PUBLICATIONS

W.G. Dauben et al., 102 Journal of the American Chemical Society, 6894-6896 (1980) (Year: 1980).*
W.G. Dauben et al., 50 Journal of Organic Chemistry, 2576-2578 (1985) (Year: 1985).*
R.M. Pagni et al., 58 Journal of Organic Chemistry, 3130-3133 (1993) (Year: 1993).*
N. Houk et al., 95 Journal of the American Chemical Society, 4094-4096 (1973) (Year: 1973).*
S.T. Handy et al., Synlett 565-567 (1995) (Year: 1995).*
I.R. Hunt et al., 117 Journal of the American Chemical Society, 1049-1056 (1995) (Year: 1995).*
S. Bouacha et al., 54 Tetrahedron Letters, 4030-4033 (2013) (Year: 2013).*
Y.V. Kharitonov et al., 39 Russian Journal of Organic Chemistry (Translation of Zhurnal Organicheskoi Khimii), 57-74 (2003) (Year: 2003).*

(Continued)

*Primary Examiner* — Alexander R Pagano
(74) *Attorney, Agent, or Firm* — Wolf, Greenfield & Sacks, P.C.

(57) ABSTRACT

The present disclosure provides methods for synthesizing cantharidin and cantharidin derivatives.

34 Claims, 3 Drawing Sheets

(56) References Cited

FOREIGN PATENT DOCUMENTS

| JP | 10-114626 | 5/1998 |
| JP | 11-319064 | 11/1999 |
| JP | 11-335303 | 12/1999 |
| JP | 2005-187330 | 7/2005 |
| JP | 20007-269693 | 10/2007 |
| JP | 2010-235471 A | 10/2010 |
| JP | 2013-507367 A | 3/2013 |
| WO | WO 2012/131238 A1 | 10/2012 |
| WO | WO 2015/027111 A1 | 2/2015 |
| WO | WO 2016/100732 A2 | 6/2016 |

OTHER PUBLICATIONS

P.A. Grieco et al., 112 Journal of the American Chemical Society, 4595-4596 (1990) (Year: 1990).*
C.E. Song et al., Chemical Communications, 1122-1123 (2001) (Year: 2001).*
J. Auge et al., 6 Synlett, 877-879 (2000) (Year: 2000).*
P. Reddy et al., 20 Bioorganic & Medicinal Chemistry Letters, 2525-2528 (2010) (Year: 2010).*
N.G. Anderson, Practical Process & Research Development (2000) (Year: 2000).*
Dauben et al., 102 J. Am. Chem. Soc., 6894-6896 (1980) (Year: 1980).*
T.K. Hollis et al., 11 Organometallics (1992) (Year: 1992).*
J. Sperry et al., 46 Tetrahedron Letters, 2789-2793 (2005) (Year: 2005).*
Invitation to Pay Additional Fees, mailed Aug. 27, 2018, in connection with PCT/US2018/O3653.
Invitation to Pay Additional Fees, mailed Sep. 20, 2018, in connection with PCT/US2018/037808.
Supplementary European Search Report, dated Aug. 8, 2018, in connection with EP 16740681.8.
Extended European Search Report, dated Mar. 10, 2017, in connection with EP 14837297.2.
International Search Report and Written Opinion, dated Nov. 20, 2014, in connection with PCT/US2014/052184.
International Search Report and Written Opinion, dated Jul. 14, 2016, in connection with PCT/US2015/066487.
International Preliminary Report on Patentability, dated Jun. 29, 2017, in connection with PCT/US2015/066487.
International Preliminary Report on Patentability, dated Aug. 3, 2017, in connection with PCT/US2016/014139.
International Search Report and Written Opinion, dated Jul. 1, 2016, in connection with PCT/US2016/014139.
Aono et al., New method for generation of thiocarbonyl ylides from bis(trimethylsilylmethyl) sulfoxides and their application to cycloadditions. Heterocycles. 1995;40(1):249-60.
Bagatell, Studies on Biological Factors in Acantholysis. J Invest Dermatol. Nov. 1964;43:357-61.
Cacchi et al., Palladium-catalyzed carbonylation of enol triflates. A novel method for one-carbon homologation of ketones to α,β-unsaturated carboxylic acid derivatives. Tetrahedron Letters. 1985;26(8):1109-1112.
Dang et al., Determination of trace cantharidin in plasma and pharmacokinetic study in beagle dogs using gas chromatography-mass spectrometry. J Anal Toxicol. Sep. 2009;33(7):384-8.
Dauben et al., Organic reactions at high pressure. Cycloadditions with furans. J. Am. Chem. Soc. 1976;98(7):1992-1993.
Dauben et al., Organic reactions at high pressure. The preparative scale synthesis of cantharidin. J. Org. Chem. 1985;50 (14):2576-2578.
Dauben et al., Simple, efficient total synthesis of cantharidin via a high-pressure Diels-Alder reaction. J. Am. Chem. Soc. 1980;102(22):6893-6894.

Dormer Laboratories, "Cantharone and Cantharone Plus" sales brochure.
Grieco et al., Dramatic rate accelerations of Diels-Alder reactions in 5 M lithium perchlorate-diethyl ether: the cantharidin problem reexamined. J. Am. Chem. Soc. 1990;112(11):4595-4596.
Handy et al., Lithium Trifluoromethanesulfonimide in Acetone or Diethyl-ether As a Safe Alternative to Lithium Perchlorate in Diethyl-ether for Effecting Diels-alder Reactions-nexpected Influence of the Counterion on Exo/endo Selectivity. Synlett 1995;1995(SI):565-567.
Magyarosy et al., Cycloaddition approach to the curing of polyimides via precursor containing thiophene-S,S-dioxide. Hetero Chem. 2006;17(7):648-652.
Mehdinia et al., Analysis of cantharidin in false blister beetles (Coleoptera: Oedemeridae) by headspace solid-phase microextraction and gas chromatography-mass spectrometry. J Chromatogr B Analyt Technol Biomed Life Sci. Oct. 1, 2011;879(27):2897-901. doi:10.1016/j.jchromb.2011.08.020. Epub Aug. 22, 2011.
Nikbakhtzadeh et al., Origin, transfer and distribution of cantharidin-related compounds in the blister beetle Hycleus scabiosae. J Venom Animals Toxins. 2012;18(1):88-96.
Rosenberg et al., Cantharidin treatment of warts at home. Arch Dermatol. Aug. 1977;113(8):1134.
Rudo et al., Cantharidin—als Potenzmittel entzaubert, aber. Chemie in unserer Zeit, 2013;47: 310-316. doi:10.1002/ciuz.201300639.
Schenck et al., Ausfuhrliche Mitteilung erfolgt an anderer Stelle. Naturwissenshaften Oct. 15, 1953; 40: 581.
Stork et al., Cantharidin. A Stereospecific Total Synthesis. J. Am. Chem. Soc. 1951;73(9):4501-4501.
Stork et al., A Stereospecific Synthesis of Cantharidin. J. Am. Chem. Soc., 1953;75(2):384-392.
Terao et al., Thiocarbonyl Ylides. VI. New Generation of Thiocarbonyl Ylides from Organosilicon Compounds Containing Sulfur and Their 1, 3-Cycloadditions. J-STAGE. 1987;35(5):1734-1740.
White et al., Dihydrothiophenes as precursors to fused quinolines, quinolones and coumarins via o-quinodimethane intermediates. Tetrahedron. 1996;52(9):3117-3134.
International Search Report and Written Opinion, dated Oct. 22, 2018, in connection with PCT/US2018/036353.
Extended European Search Report, dated Oct. 26, 2018, in connection with EP 15871116.8.
Extended European Search Report, dated Dec. 4, 2018, in connection with EP 16740681.8.
International Search Report and Written Opinion, dated Nov. 13, 2018, in connection with PCT/US2018/037808.
Invitation to Pay Additional Fees, mailed Dec. 10, 2018, in connection with PCT/US2018/054373.
International Search Report and Written Opinion, dated Apr. 3, 2019 in connection with PCT/US2018/054373.
Aitken et al., Fragmentation patterns in the gas-phase pyrolysis of some bi- and tri-cyclic sulfolanes related to the 8-thiabicyclo[4.3.0]non-3-ene 8,8-dioxide ring system . J Chem Soc. Perkin Transactions 1. 1994;16:2301-2308.
Lange et al., Synthesis of 4-carboxy-2-thiabicyclo [3.2.0] Heptan-6-ones via 3-carboxy-2,3-dihydrothiophenes: potential β-lactamase inhibitors. Tetrahedron Lett. 1985;26(15):1791-1794.
Braddock et al., Stereochemistry of the Catalysed Diels-Alder Reaction between Cyclopentadiene and Dimethyl Monothionofumarate; Soft versus Hard Lewis Acids. J. Chem. Soc. Chem. Commun. Jan. 1, 1993;16:1244-6. doi: https://doi.org/10.1039/C39930001244.
Hollis et al., Homogenous Catalysis: Transition Metal Based Lewis Acid Catalysts. Tetrahedron. 1993;49(25):5415-30. doi: https://doi.org/10.1016/S0040-4020(01)87259-8.
Huang, Catalysts for Hetero Diels-Alder Reaction of Imines. Chinese Journal of Organic Chemistry. Oct. 2003;23(10):1064-75.

* cited by examiner

COMMERCIALLY VIABLE SYNTHESIS OF CANTHARIDIN AND BIOACTIVE CANTHARIDIN DERIVATIVES

CROSS-REFERENCE

This application is a national stage filing under 35 U.S.C. § 371 of international PCT application, PCT/US2015/066487, filed Dec. 17, 2015, which claims the benefit of U.S. Provisional Patent Application Ser. No. 62/093,396, filed Dec. 17, 2014, each of which is entirely incorporated by reference herein in its entirety.

BACKGROUND

Cantharidin (1,2-Dimethyl-3,6-epoxyperhydrophthalic anhydride) is a lipophilic compound traditionally obtained from the body fluids of blister beetles, primarily of the family Meloidae. Cantharidin is an odorless, colorless, and crystalline solid at room temperature. Cantharidin is an inhibitor of protein phosphatase 2A and has vesicant activity when applied to the skin. Due to its bioactivity, cantharidin has been historically used in the treatment of various skin conditions, including the treatment of common warts and molluscum.

Chemical names: (3αR,4S,7R,7αS)-3α,7α-dimethyl-hexahydro-4,7-epoxyisobenzofuran-1,3-dione; 1,2-Dimethyl-3,6-epoxyperhydrophthalic anhydride. Common names: Cantharidin; cantharone; cantharidine; kantaridin. Structure:

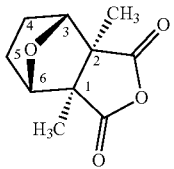

SUMMARY

The present disclosure provides methods for synthesizing cantharidin and cantharidin derivatives. Methods provided herein can enable the synthesis of cantharidin or cantharidin derivatives in a manner that may enable the commercial scale production and use of cantharidin or cantharidin derivatives, thereby advantageously minimizing or precluding the use of blister beetles for obtaining cantharidin or cantharidin derivatives.

An aspect of the present disclosure provides a method for generating a cantharidin formulation comprising cantharidin or a cantharidin derivative, the method comprising reacting a precursor of the cantharidin or cantharidin derivative to form the cantharidin formulation having the cantharidin or cantharidin derivative at an exo-to-endo ratio of at least 6:1.

In some embodiments of aspects provided herein, the exo-to-endo ratio is at least 7:1. In some embodiments of aspects provided herein, the exo-to-endo ratio is at least 8:1. In some embodiments of aspects provided herein, the exo-to-endo ratio is at least 9:1. In some embodiments of aspects provided herein, the exo-to-endo ratio is at least 10:1. In some embodiments of aspects provided herein, the exo-to-endo ratio is at least 20:1. In some embodiments of aspects provided herein, the exo-to-endo ratio is at least 100:1. In some embodiments of aspects provided herein, the formulation comprises the cantharidin derivative. In some embodiments of aspects provided herein, the reacting is conducted at a pressure less than about 100 atm. In some embodiments of aspects provided herein, the reacting is conducted at a pressure less than about 10 atm. In some embodiments of aspects provided herein, the precursor of the cantharidin or a cantharidin derivative is converted to the cantharidin or a cantharidin derivative at a yield of at least about 15%. In some embodiments of aspects provided herein, the reacting is conducted at a temperature less than about 50° C. In some embodiments of aspects provided herein, the reacting is conducted in the absence of magnesium ions. In some embodiments of aspects provided herein, the precursor is selected from compound of formula (1), (2) or (3):

(1)

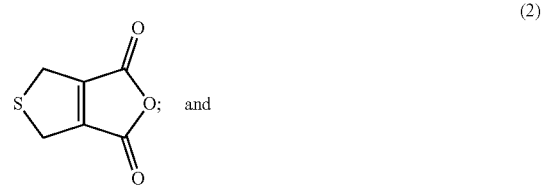

(2)

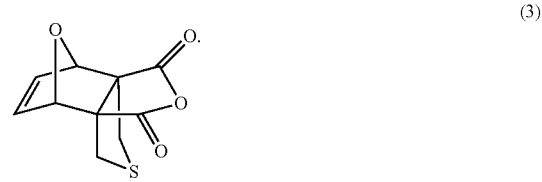 [SMILES: O=C1OC(=O)C23CSCC12C1C=CC3O1]

(3)

An aspect of the present disclosure provides a method for generating a cantharidin formulation comprising cantharidin or a cantharidin derivative, the method comprising reacting a precursor of the cantharidin or cantharidin derivative to form the cantharidin formulation having the cantharidin or cantharidin derivative, wherein the reacting is conducted (i) in the absence of diethyl ether, (ii) in the absence of a lithium or magnesium salt, and (iii) at a pressure less than about 980 atmospheres (atm).

In some embodiments of aspects provided herein, the pressure is less than about 900 atm. In some embodiments of aspects provided herein, the pressure is less than about 800 atm. In some embodiments of aspects provided herein, the pressure is less than about 700 atm. In some embodiments of aspects provided herein, the pressure is less than about 600 atm. In some embodiments of aspects provided herein, the pressure is less than about 500 atm. In some embodiments of aspects provided herein, the pressure is less than about 100 atm. In some embodiments of aspects provided herein, the pressure is less than about 10 atm. In some embodiments of aspects provided herein, the reacting is conducted with the aid of a catalyst. In some embodiments of aspects provided herein, the catalyst comprises a Lewis acid catalyst. In some embodiments of aspects provided herein, the catalyst comprises zirconium(IV). In some embodiments of aspects provided herein, the catalyst comprises bis(cyclopentadienyl)zirconium(IV) bis(trifluoromethanesulfonate)tetrahydrofuran complex. In some embodiments of aspects provided herein, the catalyst comprises aluminum chloride. In some embodiments of aspects provided herein, the catalyst comprises boron trifluoride-diethyl etherate. In some embodiments of aspects provided herein, the precursor of the cantharidin or cantharidin derivative is converted to the cantharidin or cantharidin derivative at a yield of at least about 75%. In some embodiments of aspects provided herein, the reacting is conducted at a temperature less than about 50° C. In some embodiments of aspects provided herein, the reacting is conducted in the absence of magnesium ions.

An aspect of the present disclosure provides a cantharidin formulation comprising (i) cantharidin or a cantharidin derivative, (ii) less than 0.1% diethyl ether and (iii) less than 0.1% lithium salt, wherein the cantharidin or cantharidin derivative is at an exo-to-endo ratio of at least 6:1.

In some embodiments of aspects provided herein, the exo-to-endo ratio is at least 7:1. In some embodiments of aspects provided herein, the exo-to-endo ratio is at least 8:1. In some embodiments of aspects provided herein, the exo-to-endo ratio is at least 9:1. In some embodiments of aspects provided herein, the exo-to-endo ratio is at least 10:1. In some embodiments of aspects provided herein, the exo-to-endo ratio is at least 20:1. In some embodiments of aspects provided herein, the exo-to-endo ratio is at least 100:1. In some embodiments of aspects provided herein, the cantharidin formulation includes diethyl ether. In some embodiments of aspects provided herein, the cantharidin formulation includes lithium salt.

An aspect of the present disclosure provides a cantharidin formulation comprising (i) cantharidin or a cantharidin derivative and (ii) a Lewis catalyst comprising one or more Lewis metals selected from the group consisting of Li (I), Mg (II), B (III), Al (III), Ti (IV), Zr (IV), Zn (II), Cu(I), Cu (II), Sn (II), Sn (IV), Si (IV), La (III), Sc (III), Yb (III), Eu (III), Ga (III), Sb (V), Nb (V), Fe (III), and Co (III), wherein the one or more Lewis metals are at concentration of at least about 1 part per billion (ppb).

In some embodiments of aspects provided herein, the cantharidin or cantharidin derivative is at an exo-to-endo ratio of at least 6:1. In some embodiments of aspects provided herein, the Lewis catalyst comprises Zr (IV). In some embodiments of aspects provided herein, the Lewis catalyst comprises bis(cyclopentadienyl)zirconium(IV) bis(trifluoromethanesulfonate)tetrahydrofuran complex.

An aspect of the present disclosure provides a process for preparing cantharidin or a derivative thereof, comprising: (a) providing a first compound of formula (1):

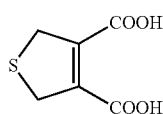
(1)

(b) forming a second compound having formula (2) from the first compound:

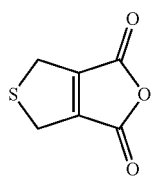
(2)

(c) performing a cycloaddition reaction on the second compound to yield a third compound having formula (3):

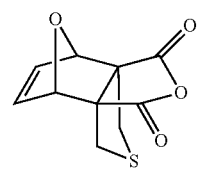
(3)

(d) generating the cantharidin or derivative thereof from the third compound.

In some embodiments of aspects provided herein, the cantharidin or derivative thereof is pharmaceutically acceptable. In some embodiments of aspects provided herein, (a) comprises generating the first compound from a fourth compound having formula (4):

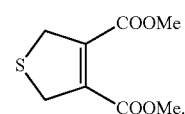
(4)

In some embodiments of aspects provided herein, the process further comprises generating the fourth compound from a fifth compound having formula (5):

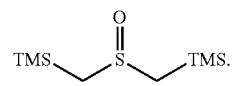
(5)

In some embodiments of aspects provided herein, the process further comprises generating the fifth compound from a sixth compound having formula (6):

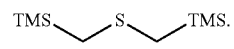
(6)

In some embodiments of aspects provided herein, the process further comprises generating the sixth compound from a seventh compound having formula (7):

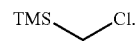
(7)

In some embodiments of aspects provided herein, the process further comprises generating the sixth compound from an eighth compound having formula (8):

$Na_2S$ (8).

In some embodiments of aspects provided herein, the process further comprises generating the fourth compound from a ninth compound having formula (9):

(9)

In some embodiments of aspects provided herein, (b) comprises subjecting the first compound to a dehydration reaction. In some embodiments of aspects provided herein, the dehydration reaction includes exposing the first compound to an acyl halide. In some embodiments of aspects provided herein, the acyl halide is acetyl chloride. In some embodiments of aspects provided herein, (c) comprises exposing the second compound to at least one Lewis acid. In some embodiments of aspects provided herein, the at least one Lewis acid is selected from Table 1. In some embodiments of aspects provided herein, the at least one Lewis acid contains a Lewis metal selected from the group consisting of Li (I), Mg (II), B (III), Al (III), Ti (IV), Zr (IV), Zn (II), Cu(I), Cu (II), Sn (II), Sn (IV), Si (IV), La (III), Sc (III), Yb (III), Eu (III), Ga (III), Sb (V), Nb (V), Fe (III), and Co (III). In some embodiments of aspects provided herein, the at least one Lewis acid is selected from magnesium perchlorate, aluminum chloride, lithium trifluoromethanesulfonate, tin (II) trifluoromethanesulfonate, bis(cyclopentadienyl)zirconium(IV) bis(trifluoromethanesulfonate)tetrahydrofuran complex, bis(cyclopentadienyl)titanium(IV) bis(trifluoromethanesulfonate), boron trifluoride diethyl etherate, and gallium(III) chloride. In some embodiments of aspects provided herein, the at least one Lewis acid is selected from copper(II) tetrafluoroborate hydrate, aluminium bromide, niobium(V) chloride, ytterbium(III) trifluoromethanesulfonate, scandium(III) trifluoromethanesulfonate, magnesium trifluoromethanesulfonate, trimethylsilyl trifluoromethanesulfonate, and copper(II) trifluoromethanesulfonate. In some embodiments of aspects provided herein, (c) comprises reacting the second compound with furan. In some embodiments of aspects provided herein, (d) comprises subjecting the third compound to a reduction reaction. In some embodiments of aspects provided herein, the reduction reaction comprises hydrogenation and desulfurization reactions performed using a single reducing agent. In some embodiments of aspects provided herein, the single reducing agent is Raney Nickel. In some embodiments of aspects provided herein, the reduction reaction comprises hydrogenation and desulfurization reactions performed using separate reducing agents. In some embodiments of aspects provided herein, the hydrogenation reaction is performed using Pd/C, Pd, PdCl$_2$, PtO$_2$, or Pt/C. In some embodiments of aspects provided herein, the desulfurization reaction is performed using a reducing agent selected from Table 2. In some embodiments of aspects provided herein, the reducing agent is Raney Nickel. In some embodiments of aspects provided herein, the reduction reaction comprises a hydrogenation reaction to yield a tenth compound having formula (10):

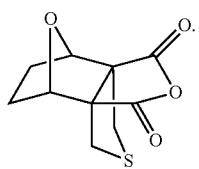

(10)

In some embodiments of aspects provided herein, the hydrogenation reaction is performed using Pd/C, Pd, PdCl$_2$, PtO$_2$, or Pt/C. In some embodiments of aspects provided herein, the process further comprises subjecting the tenth compound to an oxidation reaction. In some embodiments of aspects provided herein, the oxidation reaction is performed using at least one oxidizing agent selected from Table 3. In some embodiments of aspects provided herein, (d) comprises subjecting the third compound to an oxidation reaction. In some embodiments of aspects provided herein, the oxidation reaction is performed using at least one oxidizing agent selected from Table 3. In some embodiments of aspects provided herein, the derivative is selected from the group consisting of:

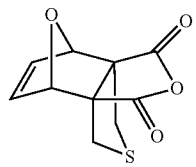

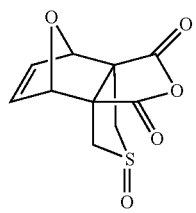

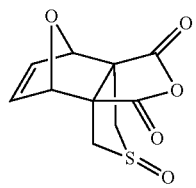

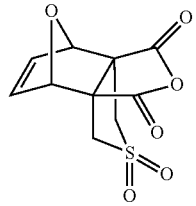

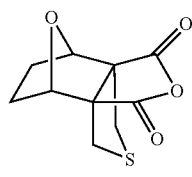

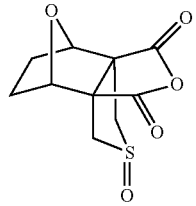

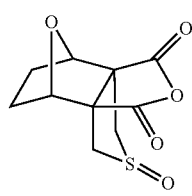

-continued

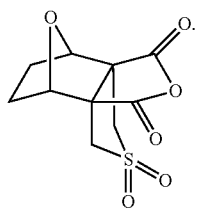

An aspect of the present disclosure provides a process, comprising: (a) providing a first compound of formula (1):

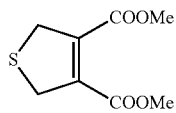
(1)

(b) forming a second compound having formula (2):

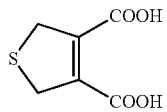
(2)

from the first compound by subjecting the first compound to a hydrolysis reaction that is performed using NaOH.

An aspect of the present disclosure provides a process, comprising: (a) providing a first compound of formula (1):

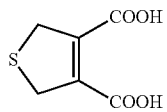
(1)

(b) forming a second compound having formula (2):

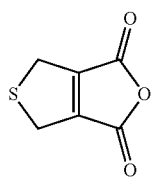
(2)

from the first compound by subjecting the first compound to a dehydration reaction that includes exposing the compound of formula (1) to an acyl halide.

In some embodiments of aspects provided herein, the acyl halide is acetyl chloride.

An aspect of the present disclosure provides a process, comprising: (a) providing a first compound of formula (1):

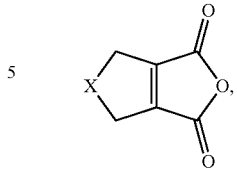
(1)

wherein X is selected from the group consisting of S, O, $CH_2$, $CHR^1$, $CR^1R^2$, NH, $NR^1$, and $NR^1R^2$, wherein the $R^1$ and $R^2$ are each independently selected from an alkyl, aryl, heteroaryl, alkoxy, amine, alcohol, and halogen or together are a carbonyl, alkenyl, imine, or oxime, wherein the $R^1$ and $R^2$ are each optionally independently substituted; and (b) forming a second compound having formula (2):

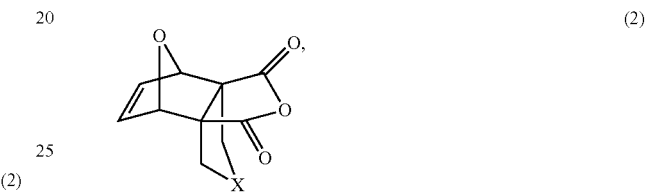
(2)

wherein X is selected from the group consisting of S, O, $CH_2$, $CHR^1$, $CR^1R^2$, NH, $NR^1$, and $NR^1R^2$, wherein the $R^1$ and $R^2$ are each independently selected from an alkyl, aryl, heteroaryl, alkoxy, amine, alcohol, and halogen or together are a carbonyl, alkenyl, imine, or oxime, wherein the $R^1$ and $R^2$ are each optionally independently substituted, from the first compound by subjecting the first compound to a cycloaddition reaction that includes exposing the first compound to at least one Lewis acid selected from the group consisting of Table 1, magnesium perchlorate, aluminum chloride, lithium trifluoromethanesulfonate, tin(II) trifluoromethanesulfonate, bis(cyclopentadienyl)zirconium(IV) bis(trifluoromethanesulfonate)tetrahydrofuran complex, bis(cyclopentadienyl)titanium(IV) bis(trifluoromethanesulfonate), boron trifluoride diethyl etherate, gallium(III) chloride, copper(II) tetrafluoroborate hydrate, aluminum bromide, niobium(V) chloride, ytterbium(III) trifluoromethanesulfonate, scandium(III) trifluoromethanesulfonate, magnesium trifluoromethanesulfonate, trimethylsilyl trifluoromethanesulfonate, and copper(II) trifluoromethanesulfonate.

In some embodiments of aspects provided herein, the at least one Lewis acid contains a Lewis metal selected from the group consisting of Li (I), Mg (II), B (III), Al (III), Ti (IV), Zr (IV), Zn (II), Cu(I), Cu (II), Sn (II), Sn (IV), Si (IV), La (III), Sc (III), Yb (III), Eu (III), Ga (III), Sb (V), Nb (V), Fe (III), and Co (III). In some embodiments of aspects provided herein, the at least one Lewis acid is selected from magnesium perchlorate, aluminum chloride, lithium trifluoromethanesulfonate, tin(II) trifluoromethanesulfonate, bis(cyclopentadienyl)zirconium(IV) bis(trifluoromethanesulfonate)tetrahydrofuran complex, bis(cyclopentadienyl) titanium(IV) bis(trifluoromethanesulfonate), boron trifluoride diethyl etherate, and gallium(III) chloride. In some embodiments of aspects provided herein, the at least one Lewis acid is selected from copper(II) tetrafluoroborate hydrate, aluminum bromide, niobium(V) chloride, ytterbium(III) trifluoromethanesulfonate, scandium(III) trifluoromethanesulfonate, magnesium trifluoromethanesulfonate, trimethylsilyl trifluoromethanesulfonate, and copper(II) trifluoromethanesulfonate. In some embodiments of aspects provided herein, X is S. In some embodiments of aspects provided herein, the cycloaddition reaction comprises reacting the first compound with furan.

An aspect of the present disclosure provides a process for preparing cantharidin, comprising: (a) providing a first compound that is selected from any one of:

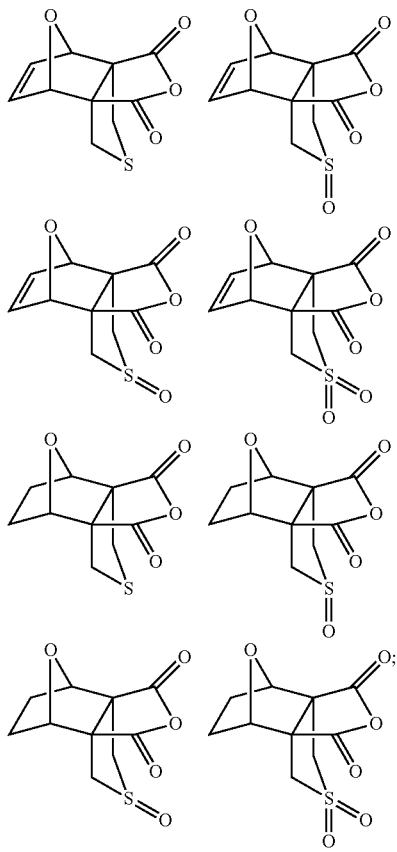

and
(b) generating the cantharidin from the first compound by subjecting the first compound to a reduction reaction that includes hydrogenation and desulfurization reactions performed using separate reducing agents, wherein the desulfurization reaction is performed using a reducing agent selected from Table 2 that is not Raney Nickel.

In some embodiments of aspects provided herein, the hydrogenation reaction is performed using Pd/C, Pd, PdCl$_2$, PtO$_2$, or Pt/C. In some embodiments of aspects provided herein, said first compound comprises

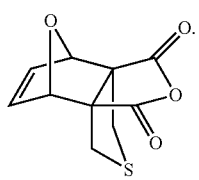

(1)

An aspect of the present disclosure provides a process, comprising: (a) providing a compound of formula (1) or (2):

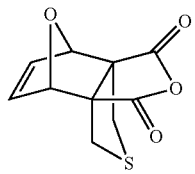

(1)

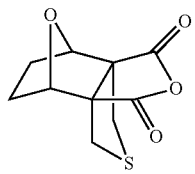

(2)

(b) forming a compound having a structure selected from the group consisting of

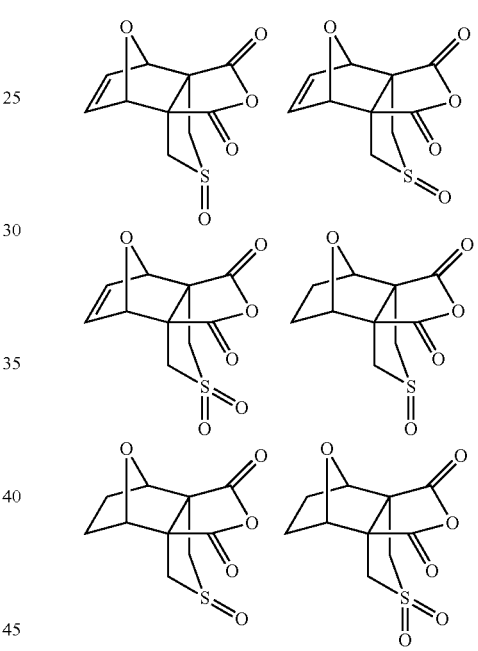

from the compound of formula (1) or (2) by subjecting the compound of formula (1) or (2) to an oxidation reaction.

In some embodiments of aspects provided herein, the oxidation reaction is performed using at least one oxidizing agent selected from Table 3.

An aspect of the present disclosure provides a process, comprising: (a) providing a compound having a structure selected from the group consisting of

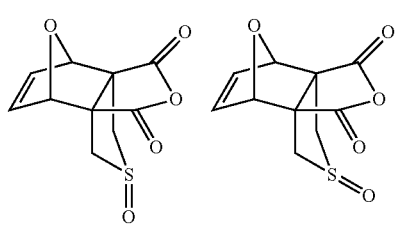

-continued

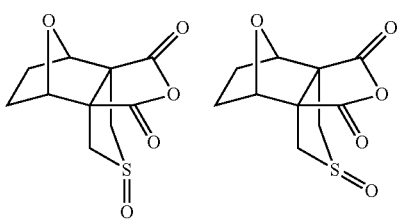

(b) forming a compound having a structure selected from the group consisting of

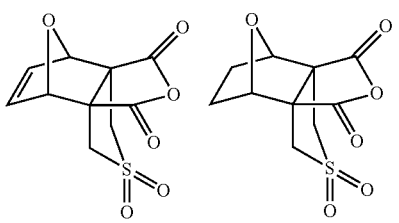

from the compound provided in (a) by subjecting the compound provided in (a) to an oxidation reaction.

In some embodiments of aspects provided herein, the oxidation reaction is performed using at least one oxidizing agent selected from Table 3.

An aspect of the present disclosure provides a composition having a structure selected from the group consisting of:

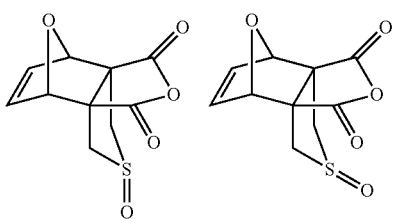

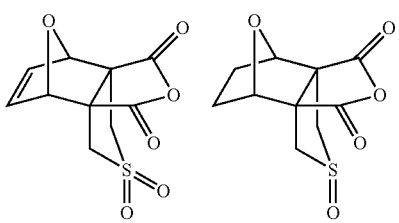

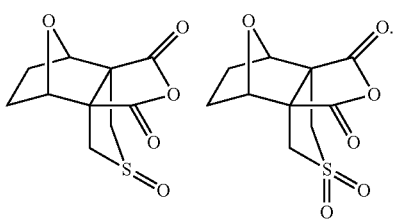

An aspect of the present disclosure provides a pharmaceutically acceptable mixture having a composition that is selected from any one of:

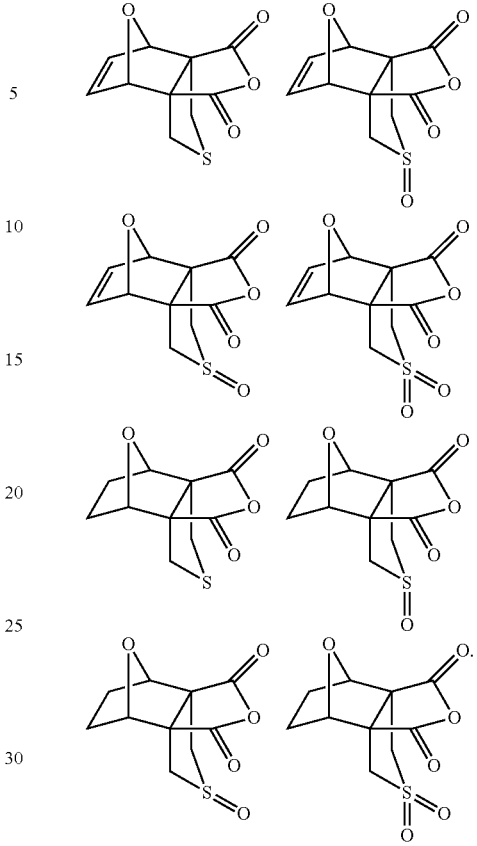

An aspect of the present disclosure provides a method of treating a subject, comprising administering to the subject a therapeutically effective amount of the pharmaceutically acceptable mixture according to embodiments provided herein.

In some embodiments of aspects provided herein, said therapeutically effective amount is effective to treat Acral fibrokeratoma, Acrodermatitus enterpathica, Acrokeratoelastoidosis, Actinic keratosis (solar keratoses), Adenoma sebaceum, Angiokeratoma, Atopic Dermatitis, Basal cell carcinoma, Benign fibrous histiocytomas, Bladder cancer, Bowen's disease, Breast cancer, Buschke-Ollendorff syndrome, Cervical cancer, Cervical dysplasia, Cherry angiomas, Chondrodermatitis nodularis chronica helicis, Common warts, Cutaneous endometriosis, Cutaneous Leukemia, Cutaneous Lymphoma, Cutaneous meningioma, Cutaneous myxoma, Darier's disease, Dermal dendrocyte hamartoma, dermatofibroma, Dermatofibrosarcoma protuberans, Eccrine angiomatous hamartoma, Ectodermal dysplasia, Epidermal inclusion cysts, Epidermal Naevi, Epithelioid cell histiocytoma, Familial myxovascular fibromas, Fungal skin disease, Granular cell tumor, Glucaonoma syndrome, Genital warts, Ichthyosis, Idiopathic guttate hypomelanosis, Infantile acropustulosis, Infantile fibromatosis, Kaposi's sarcoma, Keloid, Keratoacanthoma, Keratocyst, Knuckle pads, Lentigo, Melanoma, Microvenular hemangioma, Molluscum contagiosum, Morton's neuroma, Multifocal lymphangioendotheliomatosis, Multinucleate cell angiohistocytoma, Multiple cutaneous leiomyomas, Mycosis fungoides, Neuroma cutis, Neurothekeoma, Nevus flammeus, Nevus lipomatosus superficialis, Pachydermodactyly, Palisaded encapsulated neuroma, Parasitic skin diseases, *Pityriasis* ruba pilaris, Piloleiomyomas, Plantar warts, Plexiform fibrohistiocytic tumor, Porokeratotic eccrine ostial and Dermal duct nevus, Progressive nodular histiocytoma Psoriasis, Porokeratosis, Seborrhoeic dermatitis, Seborrheic keratosis, Rhinophyma, Solitary cutaneous leiomyoma, Spider angioma, Targetoid hemosiderotic hemangioma, Squamous cell carcinoma, Tufted angioma, Venous lake, Urticaria pigmentosa, Xanthelasmoidal mastocytosis, Zosteriform metastasis, Benign epidermal cysts, Birthmarks, Calluses, Corns, Eczema, Freckles, Moles, Pigmentation disorders, Drug induced hyperpigmentation, Dyschromatosis symmetrica hereditaria, Dyschromatosis universalis hereditaria, Familial progressive hyperpigmentation, Galli-Galli disease, Hemosiderin hyperpigmentation, Idiopathic guttate hypomelanosis, Iron metallic discoloration, leukoderma, Melasma, Mukamel syndrome, Necklace of Venus, Nevus anemicus, Nevus depigmentosus, Pallister-Killian syndrome, Phylloid hypomelanosis, Piebaldism, Pigmentatio reticularis faciei et colli, Pilar Cysts, *Pityriasis* alba, Poikiloderma of Civatte, Poikiloderma vasculare atrophicans, Postinflammatory hyperpigmentation, Progressive macular hypomelanosis, Pruritus, Reticular pigmented anomaly of the flexures, Reticulate acropigmentation of Kitamura, Riehl melanosis, Shah-Waardenburg syndrome, Shiitake mushroom dermatitis, Tar melanosis, Titanium metallic discoloration, Transient neonatal pustular melanosis, Vagabond's leukomelanoderma, Vasospastic macules, Wende-Bauckus syndrome, X-linked reticulate pigmentary disorder, Yemenite deafblind hypopigmentation syndrome, Scars, Skin tags, Tattoo removal or Vitiligo.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGS." herein), of which:

DETAILED DESCRIPTION

Figure 1:
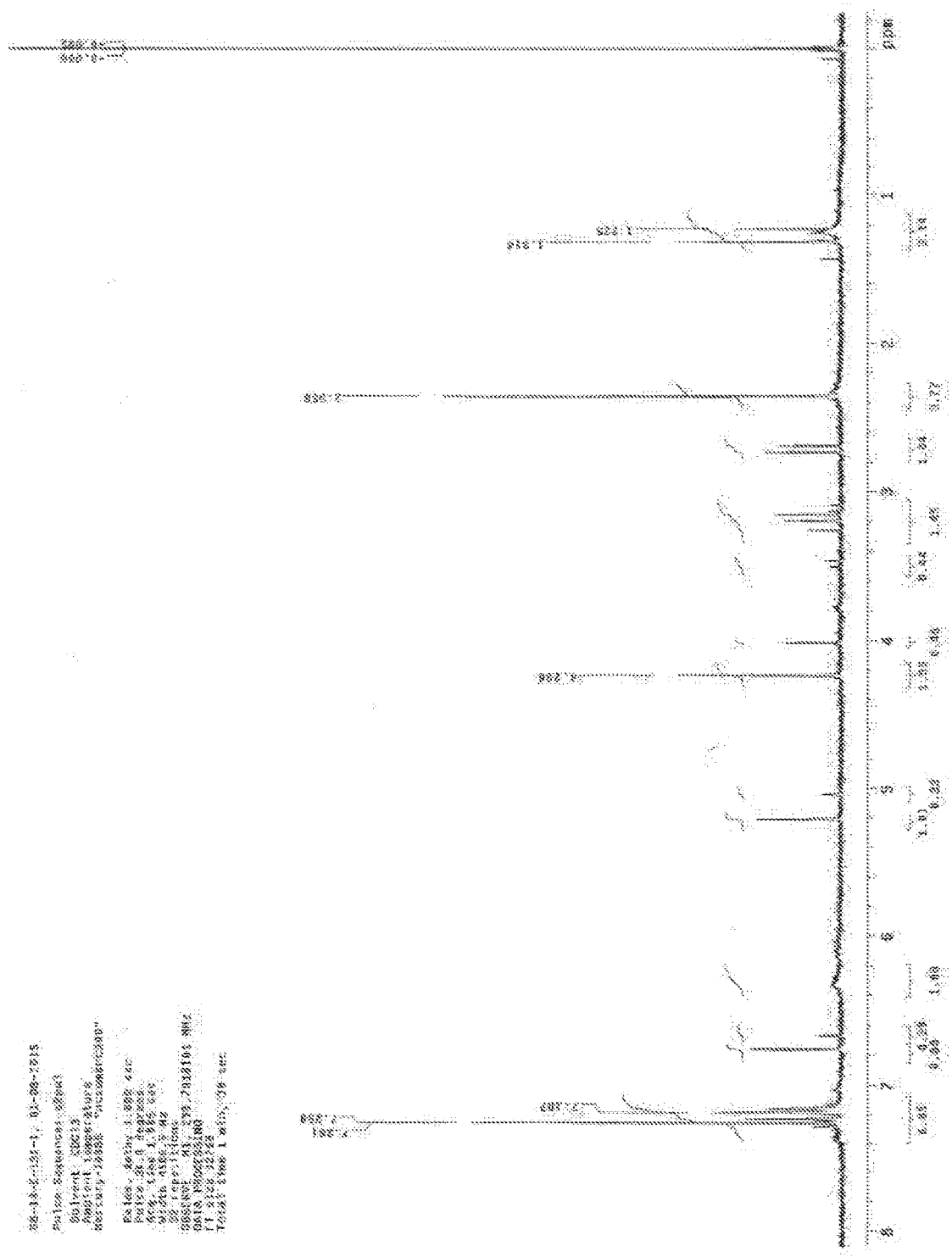
FIG. 1 shows an exemplary $^1$H NMR analysis of reaction product using aluminum chloride.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "pharmaceutically acceptable salt," as used herein, generally refers to salts derived from a variety of organic and inorganic counter ions well known in the art and include, by way of example only, base addition salts and acid addition salts. Base addition salts can be formed in cases wherein the compound comprises an acidic moiety. Acid addition salts can be formed in cases wherein the compound comprises a basic moiety. Examples of base addition salts can include alkali metal salts such as, e.g., sodium, potassium, and lithium salts, alkaline earth metal salts such as, e.g., calcium and magnesium salts, ammonium salts such as ammonium and tetraalkylammonium salts, salts with organic bases such as triethylamine, morpholine, piperidine and dicyclohexylamine; and salts with basic amino acids such as arginine and lysine. Examples of acid addition salts can include salts of organic or inorganic acids, such as hydrochloride, hydrobromide, sulfate, nitrate, formate, acetate, benzoate, maleate, fumarate, succinate, tartrate, citrate, oxalate, methanesulfonate, toluenesulfonate, aspartate, glutamate, and the like. In a compound with more than one basic moiety, more than one of the basic moieties may be converted to the salt form, including but not limited to a bis- or tris-salt. Alternatively, a compound having more than one basic moiety may form a salt at only one of the basic moieties. Pharmaceutically acceptable salts may also include the salts of the parental compounds with one or more amino acids. Any of the amino acids described above may be suitable, including the naturally-occurring amino acids that may be found as protein components, although the amino acid typically in some cases is one bearing a side chain with a basic or acidic group, e.g., lysine, arginine or glutamic acid, or a neutral group such as glycine, serine, threonine, alanine, isoleucine, or leucine.

The term "Lewis acid," as used herein, generally refers to a chemical species which is capable of accepting electrons or of reacting with a Lewis base to form a Lewis adduct. Non-limiting examples of Lewis acids include protons, acidic compounds, metal cations, metal complexes, trigonal planar species, species with a vacant or partially filled atomic or molecular orbital, and electron poor π systems. Lewis acids can include Lewis metals.

The term "aryl" (Ar), as used herein, generally refers to a polyunsaturated aromatic hydrocarbon substituent, which can be a single ring or multiple rings which can be fused together or linked covalently and can be optionally substituted. Non-limiting examples of aryl groups include phenyl, naphthyl, and biphenyl.

The term "heteroaryl," as used herein, generally refers to a polyunsaturated aromatic ring having at least one heteroatom (nitrogen, oxygen, or sulfur) in the ring chain. A heteroaryl group can be a single ring or multiple rings which can be fused together or linked covalently and can be optionally substituted. Non-limiting examples of heteroaryl groups include pyrole, pyrazole, imidazole, pyridine, pyrazine, pyrimidine, furan, thiphene, oxazole, isoxazole, purine, benzimidazole, quinoline, isoquinoline, indole, benzothiophene, and the like. When a heteroaryl group as defined herein is substituted, the substituent may be bonded to a ring carbon atom of the heteroaryl group, or to a ring heteroatom (i.e., a nitrogen, oxygen or sulfur), which has a valence which permits substitution.

The term "alkyl," as used herein, by itself or as part of another substituent, generally means a straight chain, branched chain, or cyclic hydrocarbon that may be saturated, monounsaturated, or polyunsaturated and can be optionally substituted. Examples of alkyl groups include methyl, ethyl, n-propyl, isopropyl, n-butyl, t-butyl, isobutyl, sec-butyl, pentyl, hexyl, and the like. When an alkyl group as defined herein is substituted, the substituent may be bonded to a carbon atom of the alkyl group. Non-limiting examples of substituted alkyl groups include haloalkanes, primary amines, secondary amines, tertiary amines, quaternary ammonium cations, cyclic amines, ethers, alcohols, carbonyls, imines, and oximes.

The term "alkoxy," as used herein, by itself or as part of another substituent, generally means the group O-alkyl, O-aryl, or O-heteroaryl, wherein alkyl is as defined above, to include straight, branched, or cyclic alkyl groups.

The term "halogen," as used herein, generally refers to fluorine, chlorine, bromine, and iodine.

The term "halide," as used herein, generally refers to fluoride, chloride, bromide, and iodide.

The chemical synthesis of cantharidin may be challenging. Early reported syntheses may be lengthy and low yielding processes, involve potentially dangerous operating conditions, or be commercially impractical. Some recent cantharidin syntheses have fewer steps and improve yields but may require the use of extreme reaction conditions or dangerous reagents.

Von Bruchhausen, a German chemist, attempted the synthesis of the cantharidin in 1928. See von Bruchhausen, F.; Bersch, II. W. *Arch. Pharm. Ber. Disch. Phurm. Ges.* 1928, 266, 697-702, which is entirely incorporated herein by reference. His synthetic approach was based on the following retrosynthetic analysis.

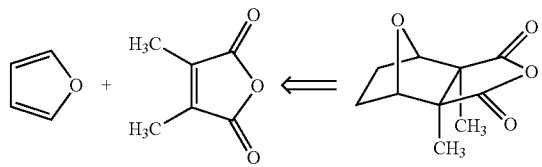

Unfortunately, the Diels-Alder reaction between the two reactants results in an equilibrium that is unfavorable to the product. As demonstrated in the following experiment, when natural cantharidin is dehydrogenated, it spontaneously undergoes a retro Diels-Alder reaction.

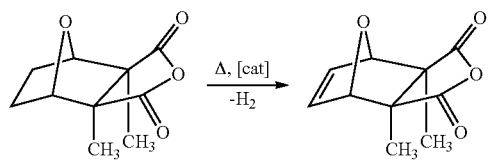

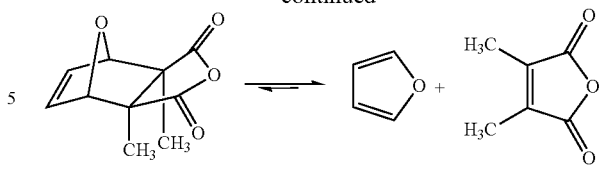

Studies have shown that the instability of the Diels-Alder product is due to the repulsion between the methyl groups carried by $C_1$ and $C_2$ and the repulsion between those methyl groups and the endo hydrogens carried by $C_4$ and $C_5$.

Stork published a synthesis of cantharidin in 1951. See Stork, G.; et al. *J. Am. Chem. Soc.* 1951, 73, 4501, which is entirely incorporated herein by reference, and Stork, G.; van Tamelen, E. E.; Friedman, L. I.; Burgstahler, A. W. *J. Am. Chem. Soc.* 1953, 75, 384, which is entirely incorporated herein by reference. This synthesis may not be economically viable. It is a lengthy, linear, multistep, and low-yielding process. On a large scale, this process may require the use of dangerous reagents that are both expensive and have the potential to create worker injury as well as unacceptable environmental disposal issues.

In 1953, Schenck published a Diels-Alder-based approach to cantharidin. See Schenck, G.; Wirtz, R. *Naturwissenshaften* 1953, 40, 531, which is entirely incorporated herein by reference. However, it still suffers from many of the issues noted above including being a long, low-yielding, linear, and multistep synthesis. Its use at a manufacturing scale may require large-scale use of toxic bromine and disposal of an environmentally noxious brominated byproduct waste stream.

In 1976, Dauben began the exploration of extreme high-pressure conditions to synthesize cantharidin. See Dauben, W. G.; Kessel, C. R.; Takemura, K. H. *J. Am. Chem. Soc.* 1980, 102, 6893-6894, which is entirely incorporated herein by reference, and Dauben, W. G.; Krabbenhoft, II. O. *J. Am. Chem. Soc.* 1976, 98, 1992-1993, which is entirely incorporated herein by reference. This synthesis requires fewer steps to prepare cantharidin in good yield, but the extreme pressures of 4-15 kilobar (kbar) necessary to successfully drive the Diels-Alder operation to completion may be dangerous at commercial scale of production. If done in multiple small batches, the process may be economically unattractive. This step may also require a significant capital investment in exotic hydraulic high-pressure production equipment as well as protective containment housing to ensure worker and community safety.

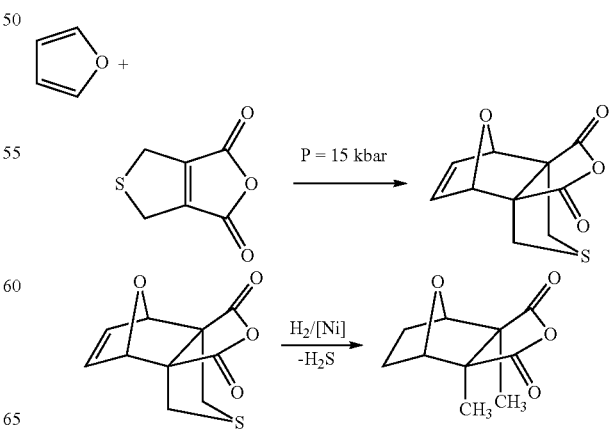

In 1990, Grieco demonstrated that the addition of 5 molar (M) lithium perchlorate in diethyl ether can facilitate the Diels-Alder reaction reported by Dauben at ambient temperatures and pressures rather than at the extreme pressures described above. See Grieco, P. A. et al. *J. Am. Chem. Soc.* 1990, 112, 4595-4596, which is entirely incorporated herein by reference. Grieco noted that this process could have utility for the synthesis of cantharidin. A relatively high yield and relatively high exo-endo Diels-Alder product ratio from this operation may make it an attractive synthesis route for large-scale production of cantharidin. Unfortunately, lithium perchlorate is a high energy content oxidizing agent that may form detonation-sensitive or highly explosive mixtures when combined with organic materials. In addition, diethyl ether is a highly volatile and flammable solvent. This reaction mixture of a high energy oxidizing agent with an easily ignited solvent may be dangerous even under controlled and small-scale conditions. Additionally, perchlorate ion may be considered a significant environmental pollutant especially when released into ground water. Perchlorate may display adverse human health effects particularly targeting iodine metabolism in the thyroid. This combination of serious safety and environmental impact issues for this synthesis makes its use as a process for commercial production of cantharidin untenable. However, the basic outline of this process for a commercial process using this short synthetic strategy remains attractive.

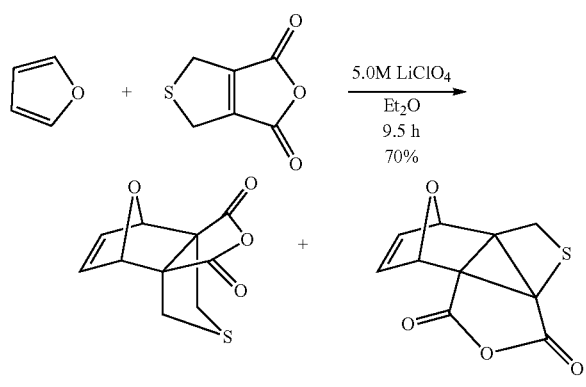

In a subsequent study by Handy in 1995, it was demonstrated that lithium trifluoromethanesulfonimide in diethyl ether or acetone also gave a good yield of Diels-Alder adduct. See Handy, S. T.; Grieco, P. A.; Mineur, C.; Ghosez, L. *Synlett* 1995, 565-567, which is entirely incorporated herein by reference. Unfortunately, this variant on the Grieco synthesis displays significant erosion in the exo-endo Diels-Alder product ratio. The exo-endo products may be difficult to separate resulting in significant losses of the desired product required for subsequent transformation to cantharidin. Such losses so late in the synthesis may adversely impact the costs of production and the ultimate profitability of the drug. Plus, the control of the increased amount of endo by-product in the production stream may add to the regulatory and quality control burden of production as well as waste disposal costs.

Despite these advances in cantharidin synthesis, a safe, simple, scalable, efficient synthesis of cantharidin at a manufacturing scale is lacking. We invent a complete synthetic process starting with available reagents that affords cantharidin under mild conditions that can be used to produce cantharidin and cantharidin analogs and derivatives that may be biologically active at a commercial scale.

The present disclosure provides methods for synthesizing cantharidin and cantharidin derivatives. Methods provided herein can enable the synthesis of cantharidin or cantharidin derivatives in a manner that may enable the commercial scale production and use of cantharidin or cantharidin derivatives.

Methods of the present disclosure can provide for synthesis of cantharidin or cantharidin derivatives without the use of diethyl ether or compounds containing diethyl ether (e.g., flexible collodion). Diethyl ether can be a highly volatile and flammable solvent, and its use in a manufacturing setting can lead to potentially unsafe or even possible explosive reaction conditions.

Methods of the present disclosure can provide for synthesis of cantharidin or cantharidin derivatives without the use of lithium salt catalysts. Lithium salts, such as lithium perchlorate or lithium trifluoromethanesulfonimide, which can be high energy content oxidizing agents that may form detonation-sensitive or highly explosive mixtures when combined with organic materials.

Methods of the present disclosure can provide for synthesis of cantharidin or cantharidin derivatives with low amounts of magnesium or no magnesium. For example, methods of the present disclosure can provide for synthesis of cantharidin or cantharidin derivatives with less than or equal to about 30%, 20%, 15%, 10%, 5%, 4%, 3%, 2%, 1%, 0.1%, 0.01%, 0.001%, or 0% magnesium ions.

Methods of the present disclosure can provide for synthesis of cantharidin formulations that contain residual amounts of catalyst, such as Lewis acid catalysts or other catalysts discussed herein, including but not limited to Li (I), Mg (II), B (III), Al (III), Ti (IV), Zr (IV), Zn (II), Cu(I), Cu (II), Sn (II), Sn (IV), Si (IV), La (III), Sc (III), Yb (III), Eu (III), Ga (III), Sb (V), Nb (V), Fe (III), and Co (III). Such catalyst materials can be present in a cantharidin formulation at a concentration of at least about 1 part per trillion (ppt), 2 ppt, 3 ppt, 4, ppt, 5 ppt, 6 ppt, 7 ppt, 8 ppt, 9 ppt, 10 ppt, 20 ppt, 30 ppt, 40 ppt, 50 ppt, 60 ppt, 70 ppt, 80 ppt, 90 ppt, 100 ppt, 200 ppt, 300 ppt, 400 ppt, 500 ppt, 600 ppt, 700 ppt, 800 ppt, 900 ppt, 1 part per billion (ppb), 2 ppb, 3 ppb, 4, ppb, 5 ppb, 6 ppb, 7 ppb, 8 ppb, 9 ppb, 10 ppb, 20 ppb, 30 ppb, 40 ppb, 50 ppb, 60 ppb, 70 ppb, 80 ppb, 90 ppb, 100 ppb, 200 ppb, 300 ppb, 400 ppb, 500 ppb, 600 ppb, 700 ppb, 800 ppb, 900 ppb, 1 part per million (ppm), 2 ppm, 3 ppm, 4, ppm, 5 ppm, 6 ppm, 7 ppm, 8 ppm, 9 ppm, 10 ppm, 20 ppm, 30 ppm, 40 ppm, 50 ppm, 60 ppm, 70 ppm, 80 ppm, 90 ppm, 100 ppm, 200 ppm, 300 ppm, 400 ppm, 500 ppm, 600 ppm, 700 ppm, 800 ppm, 900 ppm, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. Such catalyst materials can be present in a cantharidin formulation at a concentration of at most about 1 part per trillion (ppt), 2 ppt, 3 ppt, 4, ppt, 5 ppt, 6 ppt, 7 ppt, 8 ppt, 9 ppt, 10 ppt, 20 ppt, 30 ppt, 40 ppt, 50 ppt, 60 ppt, 70 ppt, 80 ppt, 90 ppt, 100 ppt, 200 ppt, 300 ppt, 400 ppt, 500 ppt, 600 ppt, 700 ppt, 800 ppt, 900 ppt, 1 part per billion (ppb), 2 ppb, 3 ppb, 4, ppb, 5 ppb, 6 ppb, 7 ppb, 8 ppb, 9 ppb, 10 ppb, 20 ppb, 30 ppb, 40 ppb, 50 ppb, 60 ppb, 70 ppb, 80 ppb, 90 ppb, 100 ppb, 200 ppb, 300 ppb, 400 ppb, 500 ppb, 600 ppb, 700 ppb, 800 ppb, 900 ppb, 1 part per million (ppm), 2 ppm, 3 ppm, 4, ppm, 5 ppm, 6 ppm, 7 ppm, 8 ppm, 9 ppm, 10 ppm, 20 ppm, 30 ppm, 40 ppm, 50 ppm, 60 ppm, 70 ppm, 80 ppm, 90 ppm, 100 ppm, 200 ppm, 300 ppm, 400 ppm, 500 ppm, 600 ppm, 700 ppm, 800 ppm, 900 ppm, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10%.

Methods of the present disclosure can provide for synthesis of cantharidin or cantharidin derivatives without the use of high pressures. High pressures can be energy intensive to produce and maintain, can necessitate the use of more expensive equipment capable of withstanding such pressures, and can be potentially explosive or otherwise dangerous. Methods of the present disclosure can provide for synthesis of cantharidin or cantharidin derivatives at a pressure of less than or equal to about 1000 atmospheres (atm), 980 atm, 975 atm, 950 atm, 925 atm, 900 atm, 875 atm, 850 atm, 825 atm, 800 atm, 775 atm, 750 atm, 725 atm, 700 atm, 675 atm, 650 atm, 625 atm, 600 atm, 575 atm, 550 atm, 525 atm, 500 atm, 475 atm, 450 atm, 425 atm, 400 atm, 375 atm, 350 atm, 325 atm, 300 atm, 275 atm, 250 atm, 225 atm, 200 atm, 175 atm, 150 atm, 125 atm, 100 atm, 75 atm, 50 atm, 45 atm, 40 atm, 35 atm, 30 atm, 25 atm, 20 atm, 15 atm, 10 atm, 9 atm, 8 atm, 7 atm, 6 atm, 5 atm, 4 atm, 3 atm, 2 atm, or 1 atm.

Methods of the present disclosure can provide for synthesis of cantharidin or cantharidin derivatives without the use of high temperatures. High temperatures can be energy intensive to produce and maintain, can necessitate the use of more expensive equipment capable of withstanding such temperatures, and can be potentially dangerous. Methods of the present disclosure can provide for synthesis of cantharidin or cantharidin derivatives at a temperature of less than or equal to about 500° C., 490° C., 480° C., 470° C., 460° C., 450° C., 440° C., 430° C., 420° C., 410° C., 400° C., 390° C., 380° C., 370° C., 360° C., 350° C., 340° C., 330° C., 320° C., 310° C., 300° C., 290° C., 280° C., 270° C., 260° C., 250° C., 240° C., 230° C., 220° C., 210° C., 200° C., 190° C., 180° C., 170° C., 160° C., 150° C., 140° C., 130° C., 120° C., 110° C., 100° C., 90° C., 80° C., 70° C., 60° C., 50° C., 40° C., 30° C., 20° C., 10° C., 0° C., –10° C., –20° C., –30° C., –40° C., –50° C., –60° C., –70° C., –80° C., –90° C., or –100° C. Methods of the present disclosure can provide for synthesis of cantharidin or cantharidin derivatives at a temperature of greater than or equal to about 500° C., 490° C., 480° C., 470° C., 460° C., 450° C., 440° C., 430° C., 420° C., 410° C., 400° C., 390° C., 380° C., 370° C., 360° C., 350° C., 340° C., 330° C., 320° C., 310° C., 300° C., 290° C., 280° C., 270° C., 260° C., 250° C., 240° C., 230° C., 220° C., 210° C., 200° C., 190° C., 180° C., 170° C., 160° C., 150° C., 140° C., 130° C., 120° C., 110° C., 100° C., 90° C., 80° C., 70° C., 60° C., 50° C., 40° C., 30° C., 20° C., 10° C., 0° C., –10° C., –20° C., –30° C., –40° C., –50° C., –60° C., –70° C., –80° C., –90° C., or –100° C. Methods of the present disclosure can provide for synthesis of cantharidin or cantharidin derivatives at a temperature of about 500° C., 490° C., 480° C., 470° C., 460° C., 450° C., 440° C., 430° C., 420° C., 410° C., 400° C., 390° C., 380° C., 370° C., 360° C., 350° C., 340° C., 330° C., 320° C., 310° C., 300° C., 290° C., 280° C., 270° C., 260° C., 250° C., 240° C., 230° C., 220° C., 210° C., 200° C., 190° C., 180° C., 170° C., 160° C., 150° C., 140° C., 130° C., 120° C., 110° C., 100° C., 90° C., 80° C., 70° C., 60° C., 50° C., 40° C., 30° C., 20° C., 10° C., 0° C., –10° C., –20° C., –30° C., –40° C., –50° C., –60° C., –70° C., –80° C., –90° C., or –100° C.

Methods for Synthesizing Cantharidin

A process for preparing cantharidin or a derivative thereof comprises providing compound (1) and generating compound (2) from compound (1).

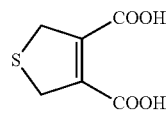

(1)

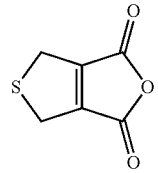

(2)

A cycloaddition reaction can then be performed on compound (2) to yield compound (3), and the cantharidin or derivative thereof can be generated from compound (3).

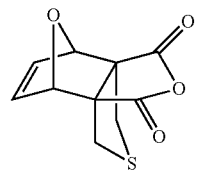

(3)

The cantharidin or derivative thereof may be pharmaceutically acceptable. In some cases, the cantharidin or derivative thereof may be prescribed and/or administered to a subject, such as for the treatment of a skin disorder, skin disease, skin inflammation, contact dermatitis, skin cancer, pre-cancerous lesion, skin infection, molluscum lesion, or wart. The cantharidin or derivative thereof can be used for treatment of a subject for conditions including but not limited to Acral fibrokeratoma, Acrodermatitus enterpathica, Acrokeratoelastoidosis, Actinic keratosis (solar keratoses), Adenoma sebaceum, Angiokeratoma, Atopic Dermatitis, Basal cell carcinoma, Benign fibrous histiocytomas, Bladder cancer, Bowen's disease, Breast cancer, Buschke-Ollendorff syndrome, Cervical cancer, Cervical dysplasia, Cherry angiomas, Chondrodermatitis nodularis chronica helicis, Common warts, Cutaneous endometriosis, Cutaneous Leukemia, Cutaneous Lymphoma, Cutaneous meningioma, Cutaneous myxoma, Darier's disease, Dermal dendrocyte hamartoma, dermatofibroma, Dermatofibrosarcoma protuberans, Eccrine angiomatous hamartoma, Ectodermal dysplasia, Epidermal inclusion cysts, Epidermal Naevi (including but not limited to naevus sebaceous, Comedone naevus, *Proteus* syndromebecker naevus), Epithelioid cell histiocytoma, Familial myxovascular fibromas, Fungal skin disease (including Lobomycosis), Granular cell tumor, Glucaonoma syndrome, Genital warts, Ichthyosis (including but not limited to Ichthyosis vulgaris, Ichthyosis lamellaria, X-linked Ichthyosis, epidermolytic hyperkeratosis, Ichthyosis acquista and keratosis palmoplantaris), Idiopathic guttate hypomelanosis, Infantile acropustulosis, Infantile fibromatosis, Kaposi's sarcoma, Keloid, Keratoacanthoma, Keratocyst, Knuckle pads, Lentigo, Melanoma, Microvenular hemangioma, Molluscum contagiosum, Morton's neuroma, Multifocal lymphangioendotheliomatosis, Multinucleate cell angiohistocytoma, Multiple cutaneous leiomyomas, Mycosis fungoides, Neuroma cutis, Neurothekeoma, Nevus flammeus, Nevus lipomatosus superficialis, Pachydermodactyly, Palisaded encapsulated neuroma, Parasitic skin diseases (including but not limited to Scabies, Pediculosis, Tungiasis, Hookwork-related cutaneous larva migrans), *Pityriasis* ruba pilaris, Piloleiomyomas, Plantar warts, Plexiform fibrohistiocytic tumor, Porokeratotic eccrine ostial and Dermal duct nevus, Progressive nodular histiocytoma Psoriasis (including but not limited to Psoriatic erytroderma, Palmoplantat psoriasis, Palmoplantar pustolosis, Generalized pustular psoriasis of Zumbusch, *Lingua geographica*), Porokeratosis (including porokeratosis of Mibelli), Seborrhoeic dermatitis, Seborrhoeic keratosis, Rhinophyma, Solitary cutaneous leiomyoma, Spider angioma, Targetoid hemosiderotic hemangioma, Squamous cell carcinoma, Tufted angioma, Venous lake, Urticaria pigmentosa, Xanthelasmoidal mastocytosis or Zosteriform metastasis. Other ailments can also be treated including Benign epidermal cysts, Birthmarks, Calluses, Corns, Eczema, Freckles, Moles, Pigmentation disorders (Drug induced hyperpigmentation, Dyschromatosis symmetrica hereditaria, Dyschromatosis universalis hereditaria, Familial progressive hyperpigmentation, Galli-Galli disease, Hemosiderin hyperpigmentation, Idiopathic guttate hypomelanosis, Iron metallic discoloration, leukoderma, Melasma, Mukamel syndrome, Necklace of Venus, Nevus anemicus, Nevus depigmentosus, Pallister-Killian syndrome, Phylloid hypomelanosis, Piebaldism, Pigmentatio *reticularis* faciei et colli, Pilar Cysts, *Pityriasis* alba, Poikiloderma of Civatte, Poikiloderma vasculare atrophicans, Postinflammatory hyperpigmentation, Progressive macular hypomelanosis, Pruritus, Reticular pigmented anomaly of the flexures, Reticulate acropigmentation of Kitamura, Riehl melanosis, Shah-Waardenburg syndrome, Shiitake mushroom dermatitis, Tar melanosis, Titanium metallic discoloration, Transient neonatal pustular melanosis, Vagabond's leukomelanoderma, Vasospastic macules, Wende-Bauckus syndrome, X-linked reticulate pigmentary disorder, Yemenite deaf-blind hypopigmentation syndrome), Scars, Skin tags, Tattoo removal or Vitiligo (including but not limited to non-segmented Vitiligo, Segmented vitiligo trichome vitiligo, Quadrichrome vitiligo, Vitiligo ponctué). The cantharidin or derivative thereof may be prescribed and/or administered in doses that are not lethal to the subject. The cantharidin or derivative thereof may be a pharmaceutically acceptable salt or co-crystal.

In some cases, Compound (1) is generated from compound (4).

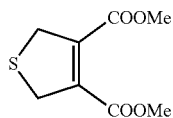

(4)

The reaction may be performed with tetrahydrofuran, water, or any mixture thereof as the solvent. The reaction may be performed in the presence of sodium hydroxide, NaOH. The reaction time may be greater than or equal to 30 seconds, 1 minute, 5 minutes, 10 minutes, 30 minutes, 1 hour, 2 hours, 3 hours, 4 hours, or 5 hours. The reaction may occur at a temperature greater than or equal to 0° C., 10° C., 20° C., 30° C., 40° C., 50° C., 60° C., 70° C., 80° C., 90° C., or 100° C. The reaction may occur at room temperature or above.

Compound (4) may be generated from compound (5).

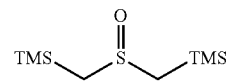

(5)

The reaction may be performed in the presence of 1,3-dimethyl-3,4,5,6-tetrahydro-2(1H)-pyrimidinone (DMPU). The reaction may be performed in the presence of dimethyl acetylenedicarboxylate, compound (6).

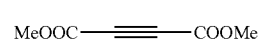

(6)

The reaction time may be greater than or equal to 30 seconds, 1 minute, 5 minutes, 10 minutes, or 30 minutes. The reaction temperature may be greater than or equal to 30° C., 40° C., 50° C., 60° C., 70° C., 80° C., 90° C., 100° C., 110° C., 120° C., 130° C., 140° C., or 150° C.

Compound (5) may be generated from compound (7).

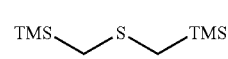

(7)

The reaction may be performed with dichloromethane (DCM) as the solvent. The reaction may be performed in the presence of a peroxy acid. The peroxy acid may be meta-chloroperoxybenzoic acid (mCPBA). The reaction time may be greater than or equal to 30 seconds, 1 minute, 5 minutes, 10 minutes, 30 minutes, or 1 hour. The reaction temperature may be less than or equal to 0° C., −10° C., −20° C., −30° C., −40° C., −50° C., −60° C., −70° C., −78° C., or −80° C.

Compound (7) may be generated from compound (8).

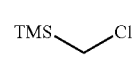

(8)

The reaction may be performed with water as the solvent. The reaction may be performed in the presence of sodium sulfide, compound (9), or a hydrate thereof.

(9)

The reaction time may be greater than or equal to 30 seconds, 1 minute, 5 minutes, 10 minutes, 30 minutes, 1 hour, 2 hours, 3 hours, 4 hours, or 5 hours. The reaction may be refluxed.

Compound (7) may be generated from sodium sulfide, compound (9), or a hydrate thereof. The reaction may be performed with water as the solvent. The reaction may be performed in the presence of compound (8). The reaction time may be greater than or equal to 30 seconds, 1 minute, 5 minutes, 10 minutes, 30 minutes, 1 hour, 2 hours, 3 hours, 4 hours, or 5 hours. The reaction may be refluxed.

Compound (4) may be generated from compound (6) and compound (5). The reaction may be performed in the presence of 1,3-dimethyl-3,4,5,6-tetrahydro-2(1H)-pyrimidinone (DMPU). The reaction may be performed in the presence of compound (5). The reaction time may be greater than or equal to 30 seconds, 1 minute, 5 minutes, 10 minutes, or 30 minutes. The reaction temperature may be greater than or equal to 30° C., 40° C., 50° C., 60° C., 70° C., 80° C., 90° C., 100° C., 110° C., 120° C., 130° C., 140° C., or 150° C.

Compound (1) may be subjected to a dehydration reaction in the process to form compound (2). The dehydration reaction may include exposing compound (1) to an acyl halide. The acyl halide may be an acyl chloride, an acyl bromide, or an acyl iodide. The acyl halide may be acetyl chloride. The acyl bromide may be acetyl bromide. The acyl iodide may be acetyl iodide. The reaction time may be greater than or equal to 30 seconds, 1 minute, 5 minutes, 10 minutes, 30 minutes, or 1 hour. The reaction may be refluxed.

Compound (2) and furan may be exposed to at least one Lewis acid in the process to form compound (3). At least one Lewis acid may contain a Lewis metal selected from the group consisting of Li (I), Mg (II), B (III), Al (III), Ti (IV), Zr (IV), Zn (II), Cu(I), Cu (II), Sn (II), Sn (IV), Si (IV), La (III), Sc (III), Yb (III), Eu (III), Ga (III), Sb (V), Nb (V), Fe (III), and Co (III). At least one Lewis acid may be selected from Table 1. At least one Lewis acid may be selected from magnesium perchlorate, aluminum chloride, lithium trifluoromethanesulfonate, tin(II) trifluoromethanesulfonate, bis(cyclopentadienyl)zirconium(IV) bis(trifluoromethanesulfonate)tetrahydrofuran complex, bis(cyclopentadienyl)titanium(IV) bis(trifluoromethanesulfonate), boron trifluoride diethyl etherate, and gallium(III) chloride. At least one Lewis acid may be selected from copper(II) tetrafluoroborate hydrate, aluminum bromide, niobium(V) chloride, ytterbium(III) trifluoromethanesulfonate, scandium(III) trifluoromethanesulfonate, magnesium trifluoromethanesulfonate, trimethylsilyl trifluoromethanesulfonate, and copper(II) trifluoromethanesulfonate. The concentration of Lewis acid may be greater than or equal to 0.01 molar (moles/liter, M), 0.02 M, 0.03 M, 0.04 M, 0.05 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2 M, 3 M, 4 M, 5 M, 6 M, 7 M, 8 M, 9 M, 10 M, 11 M, 12 M, 13 M, 14 M, 15 M, 16 M, 17 M, 18 M, 19 M, or 20 M. The reaction may be performed in the presence of furan (e.g., in furan). The reaction may be performed with acetone, toluene, benzene, xylenes, chlorobenzene, methylene chloride, ethylene dichloride, dioxane, tetrahydrofuran (THF), tert-butyl methyl ether, diisopropyl ether, 1,2-dimethoxyethane (glyme), acetonitrile, ethyl acetate, isopropyl acetate, water, or a mixture thereof as the solvent. The reaction time may be greater than or equal to 30 seconds, 1 minute, 5 minutes, 10 minutes, 30 minutes, 1 hour, 2 hours, 3 hours, 4 hours, 5 hours, 10 hours, 20 hours, 30 hours, 40 hours, 50 hours, 60 hours, 70 hours, 80 hours, 90 hours, or 100 hours. The reaction temperature may be greater than or equal to −20° C., −10° C., 0° C., 10° C., 20° C., 30° C., 40° C., 50° C., 60° C., 70° C., 80° C., 90° C., 100° C., 110° C., 120° C., 130° C., 140° C., or 150° C. The reaction may occur at room temperature or above.

Compound (2) may be reacted with furan in the process to form compound (3). The reaction may be performed in the presence of at least one Lewis acid. At least one Lewis acid may contain a Lewis metal selected from the group consisting of Li (I), Mg (II), B (III), Al (III), Ti (IV), Zr (IV), Zn (II), Cu(I), Cu (II), Sn (II), Sn (IV), Si (IV), La (III), Sc (III), Yb (III), Eu (III), Ga (III), Sb (V), Nb (V), Fe (III), and Co (III). At least one Lewis acid may be selected from Table 1. At least one Lewis acid may be selected from magnesium perchlorate, aluminum chloride, lithium trifluoromethanesulfonate, tin(II) trifluoromethanesulfonate, bis(cyclopentadienyl)zirconium(IV) bis(trifluoromethanesulfonate)tetrahydrofuran complex, bis(cyclopentadienyl)titanium(IV) bis(trifluoromethanesulfonate), boron trifluoride diethyl etherate, and gallium(III) chloride. At least one Lewis acid may be selected from copper(II) tetrafluoroborate hydrate, aluminum bromide, niobium(V) chloride, ytterbium(III) trifluoromethanesulfonate, scandium(III) trifluoromethanesulfonate, magnesium trifluoromethanesulfonate, trimethylsilyl trifluoromethanesulfonate, and copper(II) trifluoromethanesulfonate. The concentration of Lewis acid may be greater than or equal to 0.01 molar (M), 0.02 M, 0.03 M, 0.04 M, 0.05 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2 M, 3 M, 4 M, 5 M, 6 M, 7 M, 8 M, 9 M, 10 M, 11 M, 12 M, 13 M, 14 M, 15 M, 16 M, 17 M, 18 M, 19 M, or 20 M. The reaction may be performed with acetone, toluene, benzene, xylenes, chlorobenzene, methylene chloride, ethylene dichloride, dioxane, tetrahydrofuran (THF), tert-butyl methyl ether, diisopropyl ether, 1,2-dimethoxyethane (glyme), ethyl acetate, isopropyl acetate, acetonitrile, methanol, water, or a mixture thereof as the solvent. The reaction time may be greater than or equal to 30 seconds, 1 minute, 5 minutes, 10 minutes, 30 minutes, 1 hour, 2 hours, 3 hours, 4 hours, 5 hours, 10 hours, 20 hours, 30 hours, 40 hours, 50 hours, 60 hours, 70 hours, 80 hours, 90 hours, or 100 hours. The reaction temperature may be greater than or equal to −20° C., −10° C., 0° C., 10° C., 20° C., 30° C., 40° C., 50° C., 60° C., 70° C., 80° C., 90° C., 100° C., 110° C., 120° C., 130° C., 140° C., or 150° C. The reaction may occur at room temperature or above.

Compound (3) may be subjected to a reduction reaction. The reaction may be performed with ethyl acetate, isopropyl acetate, tetrahydrofuran, dioxane, diisopropyl ether, tert-butyl mryjyl ether, methylene chloride, ethylene dichloride, toluene, 1,2-dimethoxyethane, hexane, cyclohexane, acetone, acetonitrile, methanol, or water as the solvent. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. The reaction may be performed using at least one reducing agent selected from Table 2. The reaction may be performed in the presence of Raney Nickel, Ni(II)/NaBH$_4$, Co(II)/NaBH$_4$, Li/EtNH$_2$, LAH/TiCl$_3$, LAH/CuCl$_2$, Ni(II)/Zn, Ni(II)/Al, LAH/Cp$_2$Ni, Pd/C, Pd, PdCl$_2$, PtO$_2$, or Pt/C. The reaction may be performed in the presence of H$_2$. The reaction may be refluxed. In some cases, the reduction reaction may comprise hydrogenation and desulfurization reactions performed using a single reducing agent. The single reducing agent may be Raney Nickel. In other cases, the reduction reaction may comprise hydrogenation and desulfurization reactions performed using separate reducing agents. The hydrogenation reaction may be performed using Pd/C, Pd, PdCl$_2$, PtO$_2$, or Pt/C. The hydrogenation reaction may be performed in the presence of H$_2$. The desulfurization reaction may be performed using at least one reducing agent selected from Table 2. The reducing agent may be Raney Nickel. In yet other cases, the reduction reaction may comprise a hydrogenation reaction to yield compound (10).

(10)

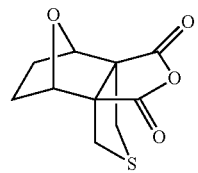

The hydrogenation reaction may be performed using Pd/C, Pd, PdCl$_2$, PtO$_2$, or Pt/C. The reaction may be performed in the presence of H$_2$.

Compound (10) may be subjected to an oxidation reaction. The oxidation reaction may be performed using at least one oxidizing agent selected from Table 3. The oxidation reaction may be performed in the presence of H$_2$O$_2$, RCO$_3$H, NaBO$_3$, KHSO$_5$, NR$_4$S$_3$O$_8$, NaOCl, or RuO$_4$.

Compound (3) may be subjecting to an oxidation reaction. The oxidation reaction may be performed using at least one oxidizing agent selected from Table 3. The oxidation reaction may be performed in the presence of H$_2$O$_2$, RCO$_3$H, NaBO$_3$, KHSO$_5$, NR$_4$S$_3$O$_8$, NaOCl, or RuO$_4$.

The derivative may be selected from the group consisting of:

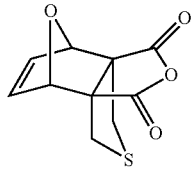
(3)

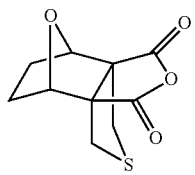
(10)

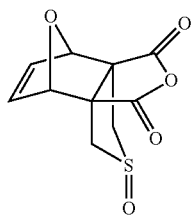
(11)

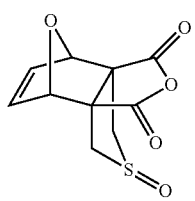
(12)

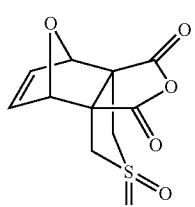
(13)

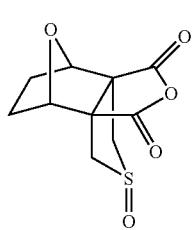
(14)

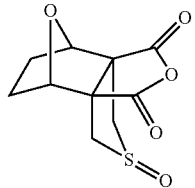
(15)

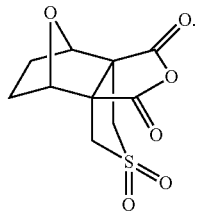
(16)

The sulfoxide may be an α or β isomer.

A process for preparing compound (1) may comprise providing and subjecting compound (4) to a hydrolysis reaction that is performed using NaOH. The reaction may be performed with tetrahydrofuran, water, or any mixture thereof as the solvent. The reaction time may be greater than or equal to 30 seconds, 1 minute, 5 minutes, 10 minutes, 30 minutes, 1 hour, 2 hours, 3 hours, 4 hours, or 5 hours. The reaction temperature may be greater than or equal to 0° C., 10° C., 20° C., 30° C., 40° C., 50° C., 60° C., 70° C., 80° C., 90° C., or 100° C. The reaction may occur at room temperature or above.

A process for preparing compound (2) may comprise providing and subjecting compound (1) to a dehydration reaction that includes exposing compound (1) to an acyl halide. The acyl halide may be an acyl chloride, an acyl bromide, or an acyl iodide. The acyl halide may be acetyl chloride. The acyl bromide may be acetyl bromide. The acyl iodide may be acetyl iodide. The reaction time may be greater than or equal to 30 seconds, 1 minute, 5 minutes, 10 minutes, 30 minutes, or 1 hour. The reaction may be refluxed.

A process may comprise providing a compound of formula (17):

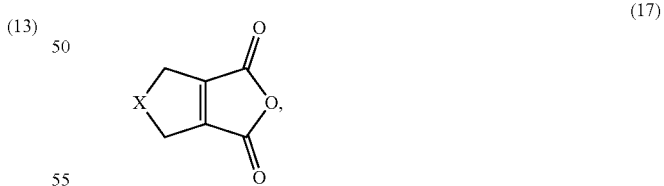
(17)

wherein X may be selected from the group consisting of S, O, CH$_2$, CHR$^1$, CR$^1$R$^2$, NH, NR$^1$, and NR$^1$R$^2$, wherein said R$^1$ and R$^2$ are each independently selected from an alkyl, aryl, heteroaryl, alkoxy, amine, alcohol, and halogen or together are a carbonyl, alkenyl, imine, or oxime, wherein said R$^1$ and R$^2$ are each optionally independently substituted, and subjecting compound (17) to a cycloaddition reaction that includes exposing compound (17) to at least one Lewis acid selected from Table 1 to form a compound having formula (18):

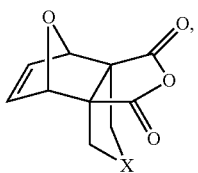

(18)

wherein X may be selected from the group consisting of S, O, CH$_2$, CHR$^1$, CR$^1$R$^2$, NH, NR$^1$, and NR$^1$R$^2$, wherein said R$^1$ and R$^2$ are each independently selected from an alkyl, aryl, heteroaryl, alkoxy, amine, alcohol, and halogen or together are a carbonyl, alkenyl, imine, or oxime, wherein said R$^1$ and R$^2$ are each optionally independently substituted. At least one Lewis acid may contain a Lewis metal selected from the group consisting of Li (I), Mg (II), B (III), Al (III), Ti (IV), Zr (IV), Zn (II), Cu(I), Cu (II), Sn (II), Sn (IV), Si (IV), La (III), Sc (III), Yb (III), Eu (III), Ga (III), Sb (V), Nb (V), Fe (III), and Co (III). At least one Lewis acid may be selected from Table 1. At least one Lewis acid may be selected from magnesium perchlorate, aluminum chloride, lithium trifluoromethanesulfonate, tin(II) trifluoromethanesulfonate, bis(cyclopentadienyl)zirconium(IV) bis(trifluoromethanesulfonate)tetrahydrofuran complex, bis(cyclopentadienyl)titanium(IV) bis(trifluoromethanesulfonate), boron trifluoride diethyl etherate, and gallium(III) chloride. At least one Lewis acid may be selected from copper(II) tetrafluoroborate hydrate, aluminum bromide, niobium(V) chloride, ytterbium(III) trifluoromethanesulfonate, scandium(III) trifluoromethanesulfonate, magnesium trifluoromethanesulfonate, trimethylsilyl trifluoromethanesulfonate, and copper(II) trifluoromethanesulfonate. The concentration of Lewis acid may be greater than or equal to 0.01 molar (M), 0.02 M, 0.03 M, 0.04 M, 0.05 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2 M, 3 M, 4 M, 5 M, 6 M, 7 M, 8 M, 9 M, 10 M, 11 M, 12 M, 13 M, 14 M, 15 M, 16 M, 17 M, 18 M, 19 M, or 20 M. The reaction may be performed with acetone, toluene, benzene, xylenes, chlorobenzene, methylene chloride, ethylene dichloride, dioxane, tetrahydrofuran (THF), tert-butyl methyl ether, diisopropyl ether, 1,2-dimethoxyethane (glyme), ethyl acetate, isopropyl acetate, acetonitrile, methanol, water, or a mixture thereof as the solvent. The reaction time may be greater than or equal to 30 seconds, 1 minute, 5 minutes, 10 minutes, 30 minutes, 1 hour, 2 hours, 3 hours, 4 hours, 5 hours, 10 hours, 20 hours, 30 hours, 40 hours, 50 hours, 60 hours, 70 hours, 80 hours, 90 hours, or 100 hours. The reaction temperature may be greater than or equal to −20° C., −10° C., 0° C., 10° C., 20° C., 30° C., 40° C., 50° C., 60° C., 70° C., 80° C., 90° C., 100° C., 110° C., 120° C., 130° C., 140° C., or 150° C. The reaction may occur at room temperature or above. X may be S. X may be O. X may be CH$_2$. The cycloaddition reaction may comprise reacting compound (17) with furan.

A process for preparing cantharidin may comprise providing and subjecting compound (3) to a reduction reaction that includes hydrogenation and desulfurization reactions performed using separate reducing agents, wherein the desulfurization reaction is performed using a reducing agent selected from Table 2. The hydrogenation reaction may be performed using Pd/C, Pd, PdCl$_2$, PtO$_2$, or Pt/C. The hydrogenation reaction may be performed in the presence of H$_2$. The reaction may be performed with ethyl acetate as the solvent. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. The reaction may be performed in the presence of Raney Nickel, Ni(II)/NaBH$_4$, Co(II)/NaBH$_4$, Li/EtNH$_2$, LAH/TiCl$_3$, LAH/CuCl$_2$, Ni(II)/Zn, Ni(II)/Al, LAH/Cp$_2$Ni, Pd/C, Pd, PdCl$_2$, PtO$_2$, or Pt/C. The reaction may be refluxed.

A process may comprise providing a compound (3) or (10) and forming a compound having a structure selected from the group consisting of compounds (11), (12), (13), (14), (15) and (16) from compound (3) or (10) by subjecting compound (3) or (10) to an oxidation reaction. The oxidation reaction may be performed using at least one oxidizing agent selected from Table 3. The oxidation reaction may be performed in the presence of H$_2$O$_2$, RCO$_3$H, NaBO$_3$, KHSO$_5$, NR$_4$S$_3$O$_8$, NaOCl, or RuO$_4$. The sulfoxide may be an α or β isomer.

A process may comprise providing a compound having a structure selected from the group consisting of compounds (11), (12), (14), and (15) and forming a compound having a structure selected from the group consisting of compounds (13) and (16) from the provided compound by subjecting the provided compound to an oxidation reaction. The oxidation reaction may be performed using at least one oxidizing agent selected from Table 3. The oxidation reaction may be performed in the presence of H$_2$O$_2$, RCO$_3$H, NaBO$_3$, KHSO$_5$, NR$_4$S$_3$O$_8$, NaOCl, or RuO$_4$. The sulfoxide may be an α or β isomer.

A composition may have a structure selected from the group consisting of:

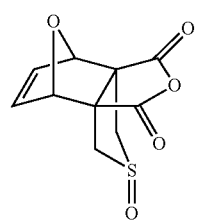

(11)

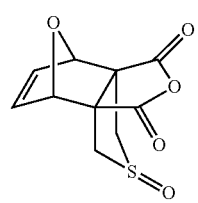

(12)

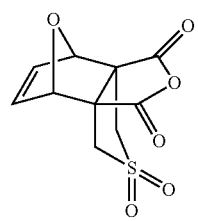

(13)

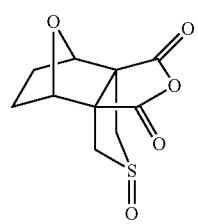

(14)

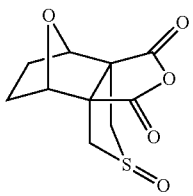
(15)

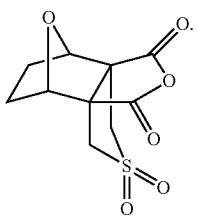
(16)

The sulfoxide may be an α or β isomer.

A pharmaceutically acceptable mixture may have a composition that is selected from any one of:

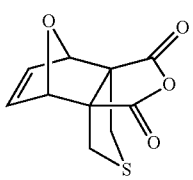
(3)

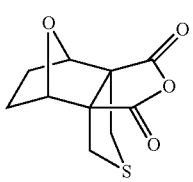
(10)

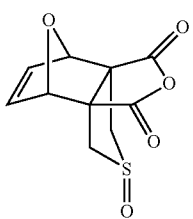
(11)

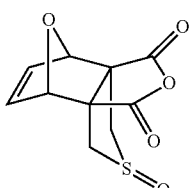
(12)

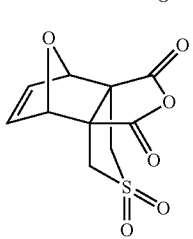
(13)

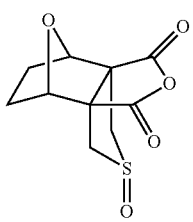
(14)

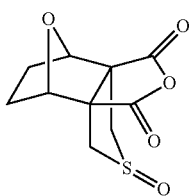
(15)

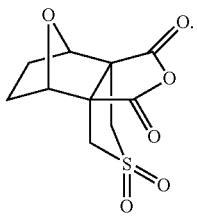
(16)

The sulfoxide may be an α or β isomer.

The synthesis of cantharidin may take place in 3 phases:

Phase 1—

This phase includes the production of compound (2) from available starting materials. Compound (2) may be synthesized starting from compound (1). Compound (2) may be synthesized starting from compound (4). Compound (2) may be synthesized starting from compound (5). Compound (2) may be synthesized starting from compound (6). Compound (2) may be synthesized starting from compound (7). Compound (2) may be synthesized starting from compound (8). Compound (2) may be synthesized starting from compound (9).

TMS⌒Cl + Na₂S  →  (water, reflux, 5 h / step 1, 95%)
    8         9

TMS⌒S⌒TMS  →  (mCPBA, -78° C., 1 h / step 2)
       7

TMS⌒S(=O)⌒TMS  +  MeOOC—≡—COOMe  →  (DMPU, 100° C., 30 min / steps 3, 60% over 2 steps)
         5

[thiophene diester structure with COOMe groups]  →  (NaOH, THF/H₂O, RT, 5 h / step 4, 83%)
         4

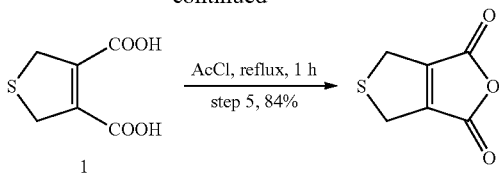

Phase 2—

This phase includes the stereo specific Diels-Alder cycloaddition of compound (2) with furan to produce compound (3).

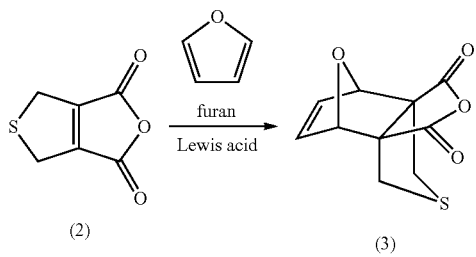

Phase 3—

This phase includes the reduction of compound (3) to produce cantharidin.

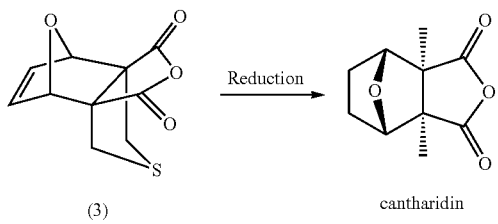 [SMILES: O=C1OC(=O)C23CSCCC12C1C=CC3O1 ; C[C@@]12C(=O)OC(=O)[C@]1(C)[C@H]1CC[C@@H]2O1]

Phase 1

Compound (2) is prepared with improved yield and improved purity to provide high quality products and improved yields that facilitate synthesis scale-up.

Phase 2

This process includes a Diels-Alder reaction of compound (2) with furan. It is unexpected that this reaction is facilitated by many Lewis acids other than lithium perchlorate or lithium trifluoromethanesulfonimide. The work of Grieco implies a uniqueness of the use of lithium perchlorate as a catalyst for this particular cycloaddition reaction. We identify a number of Lewis acids (see Table 1) that can catalyze this reaction to give high yields of the cycloadduct (3) with low levels of the undesired endo isomer and provide a significant improvement over the lithium trifluoromethanesulfonimide process. These alternative Lewis acids do not suffer from the liabilities of the diethyl ether/lithium perchlorate system described by Grieco. These Lewis acids may contain a Lewis metal selected from the group consisting of Li (I), Mg (II), B (III), Al (III), Ti (IV), Zr (IV), Zn (II), Cu(I), Cu (II), Sn (II), Sn (IV), Si (IV), La (III), Sc (III), Yb (III), Eu (III), Ga (III), Sb (V), Nb (V), Fe (III), and Co (III). These Lewis acids may be selected from Table 1. These Lewis acids may be selected from magnesium perchlorate, aluminum chloride, lithium trifluoromethanesulfonate, tin (II) trifluoromethanesulfonate, bis(cyclopentadienyl)zirconium(IV) bis(trifluoromethanesulfonate)tetrahydrofuran complex, bis(cyclopentadienyl)titanium(IV) bis(trifluoromethanesulfonate), boron trifluoride diethyl etherate, and gallium(III) chloride. These Lewis acids may be selected from copper(II) tetrafluoroborate hydrate, aluminum bromide, niobium(V) chloride, ytterbium(III) trifluoromethanesulfonate, scandium(III) trifluoromethanesulfonate, magnesium trifluoromethanesulfonate, trimethylsilyl trifluoromethanesulfonate, and copper(II) trifluoromethanesulfonate.

These Lewis acids can be used in a wide range of commercially viable manufacturing solvents including acetone, ethyl acetate, isopropyl acetate, benzene, xylenes, toluene, chlorobenzene, methylene chloride, ethylene dichloride, dioxane, THF, tert-butyl methyl ether, diisopropyl ether, 1,2-dimethoxy ethane (glyme), acetonitrile, methanol, and water. The temperature range for the various Lewis acid catalyzed Diels-Alder reaction between furan and (2) varies from −20° C. to 150° C. depending upon the specifics of the solvent and Lewis acid. This reaction can be enhanced with microwave heating or sonication depending on the specifics of the Lewis acid and solvent. Improvements in yields and exo-endo ratios in certain cases can be enhanced by the addition of trace amounts of alkali perchlorates, silver perchlorate, amines, desiccants like trialkyl aluminum reagents and zeolites, and by adding various standard free radical scavengers to the reaction.

The exo-to-endo product ratios produced by synthesis methods disclosed herein can be at least about 85:15, 86:14, 87:13, 88:12, 89:11, 90:10, 91:9, 92:8, 93:7, 94:6, 95:5, 96:4, 97:3, 98:2, 99:1, or 100:0. The percentage of exo product per total product amount can be at least about 85%, 86%, 87%, 88%, 89%, 90%, 91%, 92%, 93%, 94%, 95%, 96%, 97%, 98%, 99%, 99.5%, 99.9%, 99.99%, 99.999%, or 100%.

The product yields produced by synthesis methods disclosed herein can be at least about 5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.9%, 99.99%, 99.999%, or 100%.

TABLE 1

Lewis Acids and Companion Ligands

| Lewis Metal | Ligands bound to metal |
| --- | --- |
| Li (I) | $OCOC_7F_{15}$, $OC_6F_6$, $SbF_6$, $BF_4$, Cl, OTf, O—$SO_2Ar$, $OCOCF_3$, $OCOCH_3$ |
| Mg (II) | I, bisoxa, $BF_4$, $NTf_2$, Cl, OTf, O—$SO_2Ar$, $OCOCF_3$, $OCOCH_3$, $ClO_4$ |
| B (III) | Alkyl, OTf, F, Br, Cl, $OCOCH_3$, $OCOCF_3$, Br/$Al_2O_3$, $OCH_2CH_2O$, $OCHRCO_2$, $ArSO_2NCRCO_2$, $O(CH_2CH_3)_2$, O-biphenyl-O, O-alkyl, O—Ar |

TABLE 1-continued

Lewis Acids and Companion Ligands

| Lewis Metal | Ligands bound to metal |
| --- | --- |
| Al (III) | Alkyl, OTf, NTf$_2$, F, Br, Cl, OCOCH$_3$, OCOCF$_3$, Br/Al$_2$O$_3$, OCH$_2$CH$_2$O, ArSO$_2$NCH$_2$CH$_2$NSO$_2$Ar, O-biphenyl-O, O-alkyl, O—Ar, TfNCH$_2$CH$_2$NTf |
| Ti (IV) | NTf$_2$, OTf, O-alkyl, Cl, O-aryl, O-biphenyl-O, Cp |
| Zr (IV) | NTf$_2$, Cl, Cp, OTf, O—SO$_2$Ar, OCOCF$_3$, OCOCH$_3$ |
| Zn (II) | O-biphenyl-O, NTf$_2$, Cl, OTf, O—SO$_2$Ar, OCOCF$_3$, OCOCH$_3$ |
| Cu (I) & Cu (II) | SbF$_6$, NO$_2$/amino acids, OTf, bisoxa, BF$_4$, NalkylN, Cl, OTf, NTf$_2$, O—SO$_2$Ar, OCOCF$_3$, OCOCH$_3$ |
| Sn (II) & Sn (IV) | NTf$_2$, Cl, OTf, O—SO$_2$Ar, OCOCF$_3$, OCOCH$_3$ |
| Si (IV) | OTf, Cl |
| La (III) | TfNCH$_2$CH$_2$NTf, NTf$_2$, Cl, OTf, O—SO$_2$Ar, OCOCF$_3$, OCOCH$_3$ |
| Sc (III) | Cl, OTf, O—SO$_2$Ar, OCOCF$_3$, OCOCH$_3$ |
| Yb (III) | O-biphenyl-O, NTf$_2$, Cl, OTf, O—SO$_2$Ar, OCOCF$_3$, OCOCH$_3$ |
| Eu (III) | Cl, OTf, fod, O—SO$_2$Ar, OCOCF$_3$, OCOCH$_3$ |
| Ga (III) | NTf$_2$, Cl, OTf, O—SO$_2$Ar, OCOCF$_3$, OCOCH$_3$ |
| Sb (V) | Cl, OTf, O—SO$_2$Ar, OCOCF$_3$, OCOCH$_3$ |
| Nb (V) | Cl, OTf, O—SO$_2$Ar, OCOCF$_3$, OCOCH$_3$ |
| Fe (III) | Cl, OTf, O—SO$_2$Ar, OCOCF$_3$, OCOCH$_3$ |
| Co (III) | Cl, OTf, O—SO$_2$Ar, OCOCF$_3$, OCOCH$_3$ | where

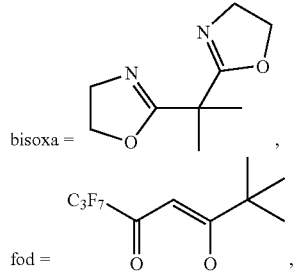

$NTf_2 = [(CF_3SO_2)_2N]^-$, $OTf = CF_3SO_3^-$, and $Tf = CF_3SO_2$

For example, a 0.01 M to 20 M solution of at least one Lewis Acid in diethyl ether can be added to a stirred mixture of furan and compound (2) at room temperature under argon atmosphere. At least one Lewis acid may contain a Lewis metal selected from the group consisting of Li (I), Mg (II), B (III), Al (III), Ti (IV), Zr (IV), Zn (II), Cu(I), Cu (II), Sn (II), Sn (IV), Si (IV), La (III), Sc (III), Yb (III), Eu (III), Ga (III), Sb (V), Nb (V), Fe (III), and Co (III). At least one Lewis acid may be selected from Table 1. At least one Lewis acid may be selected from magnesium perchlorate, aluminum chloride, lithium trifluoromethanesulfonate, tin(II) trifluoromethanesulfonate, bis(cyclopentadienyl)zirconium (IV) bis(trifluoromethanesulfonate)tetrahydrofuran complex, bis(cyclopentadienyl)titanium(IV) bis(trifluoromethanesulfonate), boron trifluoride diethyl etherate, and gallium(III) chloride. At least one Lewis acid may be selected from copper(II) tetrafluoroborate hydrate, aluminum bromide, niobium(V) chloride, ytterbium(III) trifluoromethanesulfonate, scandium(III) trifluoromethanesulfonate, magnesium trifluoromethanesulfonate, trimethylsilyl trifluoromethanesulfonate, and copper(II) trifluoromethanesulfonate. The resulting mixture can be stirred for 1 to 100 hours or more and water added. The mixture can be extracted with MTBE. The crude material can be dissolved in small amount of dichloromethane, passed through a pad of silica, and washed with dichloromethane. The combined filtrates can be evaporated to afford a white solid with mixtures of product and starting material that can be used in the next step without further purification or purified and stored.

Phase 3

The final step of the synthesis of cantharidin from (3) involves reduction of the carbon-carbon double bond and desulfurization. The original Dauben procedure for transformation of (3) directly to cantharidin using a single step reduction of the olefin and desulfurization with Raney nickel is subject to specific difficulties involving the consistent production of the Raney nickel catalyst that gives a high and consistent yield of cantharidin at production scale. One major issue with this step can be the generation of unstable olefin (19) that can readily undergo a retro-Diels-Alder reaction leading to serious losses of product at a late stage in the synthesis. We identify a specific commercially available Raney nickel catalyst that minimizes losses resulting from delayed olefin hydrogenation prior to desulfurization.

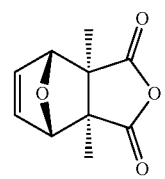

(19)

Alternatively, compound (3) can be efficiently hydrogenated using standard palladium or platinum catalysts and low-pressure hydrogen to give product (10) in high yield. Subsequent desulfurization of (10) with at least one reducing agent listed in Table 2 gives cantharidin in excellent yield. This scalable two-step process can greatly increase the quality and yield of product cantharidin and minimize or avoid the use and potential health and environmental hazards of using Raney nickel or other similar sponge-metal catalysts. This process is a significant process improvement over the one-step reduction process using Raney nickel.

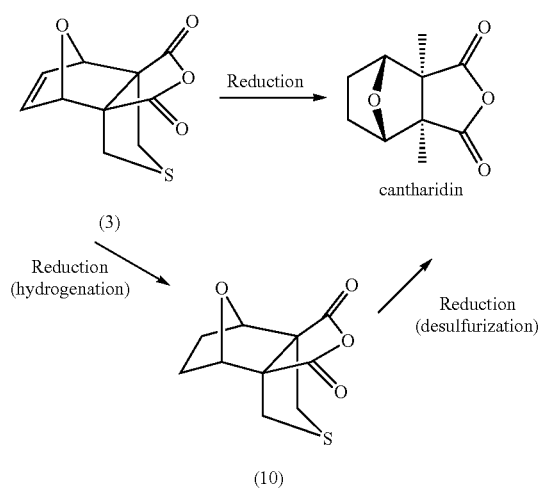 [SMILES: O=C1OC(=O)C23CSCCC12C1C=CC3O1 ; C[C@@]12C(=O)OC(=O)[C@]1(C)[C@H]1CC[C@@H]2O1 ; O=C1OC(=O)C23CSCCC12C1CCC3O1]

TABLE 2

Desulfurization Reagents
Raney Nickel

Ni(II)/NaBH$_4$
Co(II)/NaBH4
Li/EtNH$_2$
LAH/TiCl$_3$
LAH/CuCl$_2$
Ni(II)/Zn or Al
LAH/Cp$_2$Ni

The typical solvents for desulfurization reactions can be alcohols, ethers, ester-based solvents and water or various mixtures of these solvents. Reaction temperatures can be from −20° C. to 100° C. depending on the specific solvent. These reactions can be facilitated with the aid of sonication or microwave heating.

For example, a slurry of at least one desulfurization agent listed in Table 2 in water can be added to a solution of compound (3) in ethyl acetate. The mixture can be refluxed for 1 to 10 hours, filtered through a pad of celite while hot, and washed with hot acetone. The filtrate can be evaporated to dryness, and the crude material can be triturated in ethyl acetate. The solid obtained can be filtered to obtain cantharidin as white solid.

Synthesis of Cantharidin Derivatives

The described procedures can also be used to make cantharidin derivatives and cantharidin analogues that may have bioactivity. These molecules include but are not limited to sulfides (3) and (10); their respective sulfoxide derivatives (11), (12), (14), and (15); and their respective sulfone derivatives (13) and (16). Oxidation of (3) or (10) or a mixture thereof with at least one of the reagents listed in Table 3 may yield at least one of sulfoxides (either a or β isomer) (11), (12), (14), and (15) or sulfones (13) and (16) or a mixture thereof. Oxidation of at least one of (11), (12), (14), and (15) or a mixture thereof with at least one of the reagents listed in Table 3 may yield at least one of sulfones (13) and (16). The sulfide, sulfoxide, and sulfone derivatives may be biologically active. The sulfide, sulfoxide, and sulfone derivatives may be pharmaceutically acceptable. The sulfide, sulfoxide, and sulfone derivatives may be a pharmaceutically acceptable salt.

TABLE 3

| Oxidizing agents (by Class) | |
|---|---|
| Sulfoxides | Sulfones |
| H$_2$O$_2$ | H$_2$O$_2$ |
| RCO$_3$H | RCO$_3$H |
| (CH$_3$)CO$_2$ | |
| t-BuO$_2$H | |
| NaBO$_3$ | NaBO$_3$ |
| KHSO$_5$ | KHSO$_5$ |
| NaBrO$_2$ | NR$_4$S$_3$O$_8$ |
| NaIO$_4$ | |
| N$_2$O$_4$ | NaOCl |
| HNO$_3$ | |
| ArIO | RuO$_4$ |
| ArI(OAc)$_2$ | |
| SO$_2$Cl$_2$ | |
| t-BuOCl | |
| MnO$_2$ | |
| H$_2$CrO$_4$ | |
| Ti(IV)/t-BuO$_2$H | | where R is independently selected from an alkyl, aryl, heteroaryl, alkoxy, amine, alcohol, and halogen and is optionally substituted Reaction solvents include water, alcohols, methylene chloride and other halogenated hydrocarbons, ethers, water, toluene, benzene, xylene, acetone and similar ketone solvents, organic acids, ethyl acetate, isopropyl acetate, acetonitrile or various mixtures of these solvents. These reactions can be facilitated with sonication, microwave irradiation and/or the addition of phase transfer salts.

For example, a solution of compound (3) in ethyl acetate can be hydrogenated in the presence of Pd/C under hydrogen atmosphere for 1 to 72 hours. The mixture can be filtered through a pad of celite and washed with ethyl acetate. The solid obtained can be dissolved in a small amount of dichloromethane and purified by silica gel chromatography to afford compound (10), a white crystalline solid. Compound (3) or compound (10) or a mixture thereof can then be oxidized with at least one oxidizing agent listed in Table 3 to generate either a sulfoxide or sulfone product or a mixture thereof.

Some reactions may be modified from Chem. Pharm. Bull. 1987, 35(5), 1734-1740; Heteroatom Chemistry 2006, Volume 17, Number 7, 648-652; J. Am. Chem. Soc. 1990, 112, 4595-4596; J. Org. Chem. 1985, 50, 2576-2578; and J. Am. Chem. Soc. 1980, 102, 6893-6894.

The following Scheme is followed and information on each step is provided at the end:

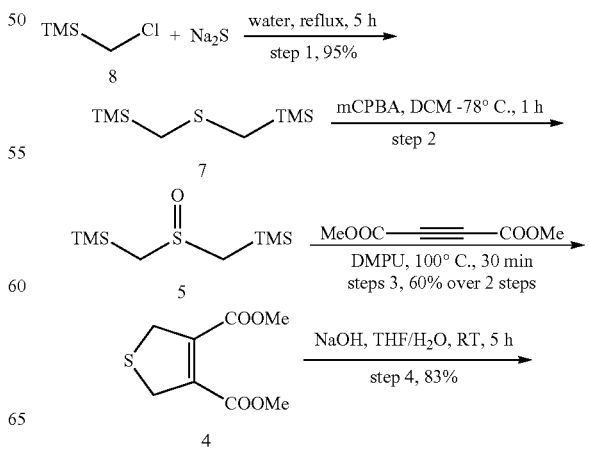

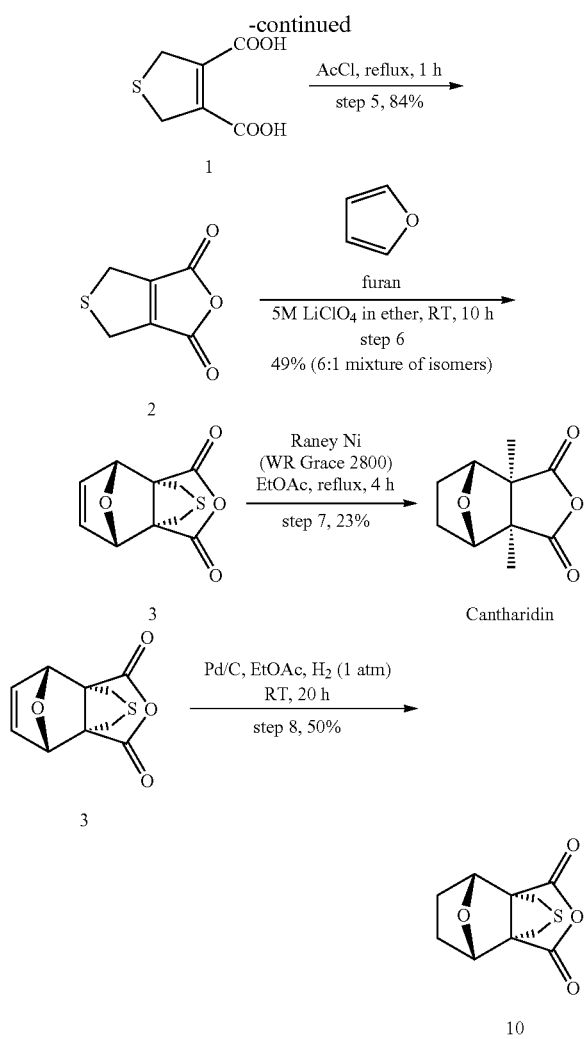

saturated NaHCO₃, and the layers are separated. The organic layer is dried over MgSO₄, filtered, and concentrated under reduced pressure at 5-10° C. bath temperature to afford the sulfoxide product (5) quantitatively. The crude product is taken directly to the next step without purification.

Example 3: Dimethyl 2,5-Dihydrothiophene-3,4-dicarboxylate, Compound (4)

Experimental Methods for Step 3:

A mixture of compound (5) (32.0 g, 145.6 mmol) and dimethyl acetylenedicarboxylate (10.34 g, 72.8 mmol) in DMPU (1 vol) is added to a preheated solution of DMPU at 100° C. The resulting mixture is stirred at 100° C. for 30 minutes and then poured onto ice water (250 g). The mixture is extracted with dichloromethane (500 mL), dried over MgSO₄, filtered, and concentrated under reduced pressure. The crude material is purified by column chromatography to afford the ester (4) (8.5 g, 60.0%) as a light yellow oil.

Example 4: Compound (1)

Experimental Methods for Step 4:

Compound (4) (8.5 g, 42 mmol) is dissolved in a 1:1 mixture of THF and water (85 mL, 10 vol). NaOH (6.73 g, 168.3 mmol) is added at room temperature, and the resulting mixture is stirred for 4 hours at room temperature. After confirming the disappearance of starting material by TLC, the mixture is washed with twice with MTBE to remove unreacted materials and impurities. The pH of the aqueous solution is adjusted to ~4 with 1N HCl solution and extracted with ethyl acetate (2×100 mL). The combined organic layers are dried over MgSO₄, filtered, and concentrated under reduced pressure to afford product (1) as an off-white solid (6.05 g, 83%).

Example 5: 2,2,4,4-Tetrahydrothiophene-3,4-dicarboxylic anhydride, Compound (2)

Experimental Methods for Step 5:

A solution of compound (1) (6.05 g, 34.7 mmol) in acetyl chloride (30 mL, 5 vol) is refluxed for 1 hour. The reaction mixture is concentrated under reduced pressure and dissolved in a small amount of dichloromethane and triturated with heptanes. The resulting solid is filtered and dried overnight under high vacuum to afford product (2) (4.47 g, 84%) as an off-white solid.

Example 6: Compound (3)

Experimental Methods for Step 6:

A 5.0 M solution of LiClO₄ in diethyl ether (25.15 g, 235.6 mmol) is added to a stirred mixture of furan (5.45 g, 80.1 mmol) and compound (2) (2.5 g, 16.0 mmol) at room temperature under argon atmosphere. The resulting mixture is stirred for 10 hours, and water (80 ml) is added. The mixture is extracted with MTBE (3×50 mL). The crude material is dissolved in a small amount of DCM and passed through a pad of silica washed with dichloromethane. The combined filtrates are evaporated to afford a white solid with 75:25 mixtures of product and starting material which is used in the next step without further purification (1.77 g, 49%).

Example 1: Bis(trimethylsilylmethyl) sulfide, compound (2)

Experimental Methods for Step 1:

Chloromethyltrimethylsilane (50.0 g, 407.5 millimoles (mmol)) and tetrabutylammonium iodide (7.52 g, 20.3 mmol) are added to an aqueous solution of sodium sulfide hydrated (23.1 g, 203.5 mmol) in 100 mL water. The mixture is stirred at reflux temperature for 5 hours and then cooled to room temperature. The organic layer is separated, and the aqueous layer is extracted with MTBE (2×50 mL). The combined solutions are dried over MgSO₄, filtered, and concentrated under reduced pressure. The crude product (7) afforded as a light yellow oil is directly taken to next step without further purification (40 g, 95%).

Example 2: Compound (3)

Experimental Methods for Step 2:

Compound (7) (30 g, 145.2 mmol) in DCM (15 vol) is cooled to −78° C. m-CPBA (predried over molecular sieves 4A) in DCM (5 vol) is added slowly. The mixture is stirred at −78° C. for 1 hour. Disappearance of the starting material is confirmed from TLC analysis, and the mixture is warmed to 0° C. The mixture is added to ice cold solution of

Example 7: Cantharidin

Experimental Methods for Step 7:

To a solution of compound (3) (0.25 g, 1.11 mmol) in ethyl acetate (10 mL) is added Raney Ni type 2800 (Aldrich, 2.5 g in 4 mL water) slurry in water. The mixture is refluxed for 4 hours, filtered through a pad of celite while hot, and washed with hot acetone (40 mL). The filtrate is evaporated to dryness, the crude product is triturated in ethyl acetate, and the solid obtained is filtered to obtain cantharidin as a white solid (50 mg, 23%).

Example 8: Compound (10)

Experimental Methods for Step 8:

A solution of compound (3) (0.4 g, 1.78 mmol) in ethyl acetate (10 mL) is hydrogenated in the presence of 10% Pd/C (40 mg) under hydrogen atmosphere for 4 hours. TLC shows only partial conversion. An additional 10% of the catalyst (40 mg) is added, and the mixture is stirred overnight for complete conversion. The mixture is filtered through a pad of celite and washed with ethyl acetate. The solid obtained is dissolved in a small amount of dichloromethane and purified by silica gel chromatography to afford compound (10) as a white crystalline solid (0.2 g, 50%).

Example 9: Diels-Alder Catalysts

Experiments were conducted to determine a two or three step synthesis for cantharidin without the use of lithium perchlorate, resulting in a final reduction/desulfurization reaction of:

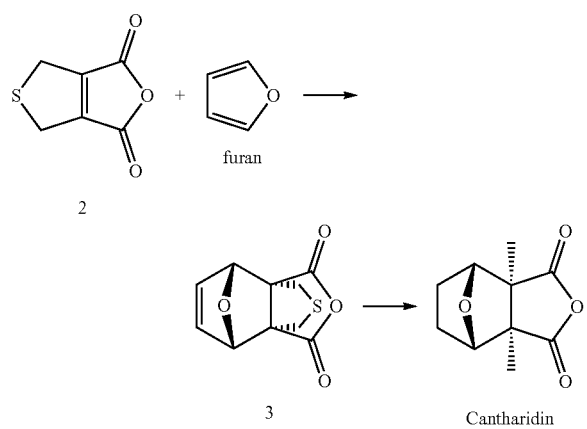

The original Diels-Alder (DA) chemistry using lithium perchlorate (LiClO$_4$) is:

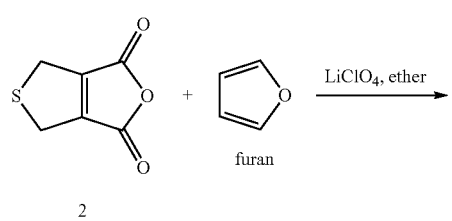

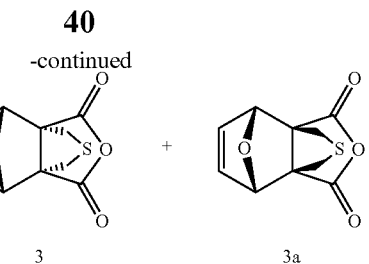

The original DA chemistry between intermediate 2 and furan was performed in ether in the presence of large excess lithium perchlorate (15.6 equiv). This process can have several drawbacks, including use of a large excess of lithium perchlorate, the explosive characteristics of lithium perchlorate, need to dry lithium perchlorate (e.g., 48 hours at 140° C.) which can be difficult and hazardous at scale-up, high volatility and flammability of the solvent ether, and the production of a mixture of two isomers 3 and 3a rather than only the desired isomer 3.

The DA reaction was investigated with 41 Lewis acid catalysts. Table 4 shows the catalyst name and the results from the DA chemistry. A total of 41 Lewis Acid catalysts were tested for the Diels Alder reaction between intermediate 2 and furan as shown in Table 4 below. 2 equiv of catalyst were used for 25 mg scale reactions in screw cap vials. 0.3 mL of drying agent trimethylaluminum was used in each reaction. The reaction was performed in toluene at room temperature and analyzed by thin liquid chromatography (TLC) after 5 hours and 20 hours, at which point it is considered complete.

TABLE 4

Diels-Alder chemistry results for 41 Lewis acid catalysts

| | Catalyst | Product observed in TLC - 5 h | Product observed in TLC - 20 h |
|---|---|---|---|
| 1 | Copper tetrafluoroborate hydrate | Not observed | Not prominent |
| 2 | Aluminum bromide | Not observed | Not prominent |
| 3 | Niobium chloride | Not observed | Not prominent |
| 4 | Magnesium iodide | Not observed | Not observed |
| 5 | Lanthanum triflate | Not observed | Not observed |
| 6 | Lithium tetrafluoroborate | Not observed | Not observed |
| 7 | Cobalt chloride | Not observed | Not observed |
| 8 | Ytterbium triflate | Not observed | Not prominent |
| 9 | Bis(trifluoromethane)sulfonimide Li-salt | Not observed | Not observed |
| 10 | Tin triflate | Less prominent | Prominent |
| 11 | Scandium triflate | Not observed | Not prominent |
| 12 | Bis(cyclopentadienyl)titanium(IV) dichloride | Not observed | Not observed |
| 13 | Iron chloride | Not observed | Not observed |
| 14 | Magnesium perchlorate | Not observed | Not prominent |
| 15 | Bis(cyclopentadienyl)zirconium(IV) dichloride | Not observed | Not observed |
| 16 | Bis(cyclopentadienyl)zirconium triflate-THF complex | Not observed | Prominent |
| 17 | Magnesium triflate | Not observed | Not prominent |
| 18 | Li-trifluoroacetate | Not observed | Not observed |
| 19 | Eu(fod)$_3$ complex | Not observed | Not observed |
| 20 | Copper triflate | Not observed | Not prominent |
| 21 | Lithium triflate | Not observed | Not prominent |
| 22 | Bis(cyclopentadienyl)titanium triflate | Not observed | Prominent |
| 23 | Titanium tetrachloride-THF complex | Not observed | Not observed |
| 24 | Zirconium(IV) chloride | Not observed | Not observed |
| 25 | Aluminum chloride | Not observed | Not observed |
| 26 | Galium chloride | Not observed | Prominent |

TABLE 4-continued

Diels-Alder chemistry results for 41 Lewis acid catalysts

| Catalyst | Product observed in TLC - 5 h | Product observed in TLC - 20 h |
|---|---|---|
| 27 Boron trifluoride-diethyl etherate complex | Not observed | Prominent |
| 28 Trimethyl borate | Not observed | Not observed |
| 29 Tin chloride | Not observed | Not observed |
| 30 Zinc chloride | Not observed | Not observed |
| 31 Titanium(IV) isopropoxide | Not observed | Not observed |
| 32 Antimony chloride | Not observed | Not observed |
| 33 Isopropoxyboronic acid pinacol ester | Not observed | Not observed |
| 34 Titanium diisopropoxide dichloride | Not observed | Not observed |
| 35 Trimethylsilyl triflate | Not observed | Not prominent |
| 36 Boron tribromide | Not observed | Not observed |
| 37 Lithium chloride | Not observed | Not observed |
| 38 Diethyl aluminum chloride | Not observed | Not observed |
| 39 Ethyl aluminum dichloride | Not observed | Not observed |
| 40 Dimethyl aluminum chloride | Not observed | Not observed |
| 41 Dibutylboron triflate | Not observed | Not observed |

Several positive reactions were observed out of these 41 reactions shown above. Prominent product peaks were observed for tin triflate, bis(cyclopentadienyl)zirconium triflate-THF complex, bis(cyclopentadienyl)titanium triflate, galium chloride, and boron trifluoride-diethyl etherate complex. Minor product was observed for copper tetrafluoroborate hydrate, aluminum bromide, niobium chloride, ytterbium triflate, scandium triflate, magnesium perchlorate, magnesium triflate, copper triflate, lithium triflate, and trimethylsilyl triflate. For magnesium perchlorate, 5 equiv afforded better results in line with lithium perchlorate used previously.

The DA reaction was repeated using several catalysts: aluminium chloride, lithium triflate, tin triflate, bis(cyclopentadienyl)zirconium triflate-THF complex, bis(cyclopentadienyl)titanium triflate, and boron trifluoride-diethyl etherate complex. Magnesium perchlorate was excluded as it can have many of the same drawbacks as lithium perchlorate. Two sets of reactions were performed to compare the effect of the drying agent; the first set of reactions was performed in the presence of trimethyl aluminum, and the second set of reactions was performed in the absence of trimethyl aluminum. The reactions were performed at 25 mg scale of compound 2 in the presence of excess furan and 2 equiv of Lewis acid (LA).

Figure 2A:
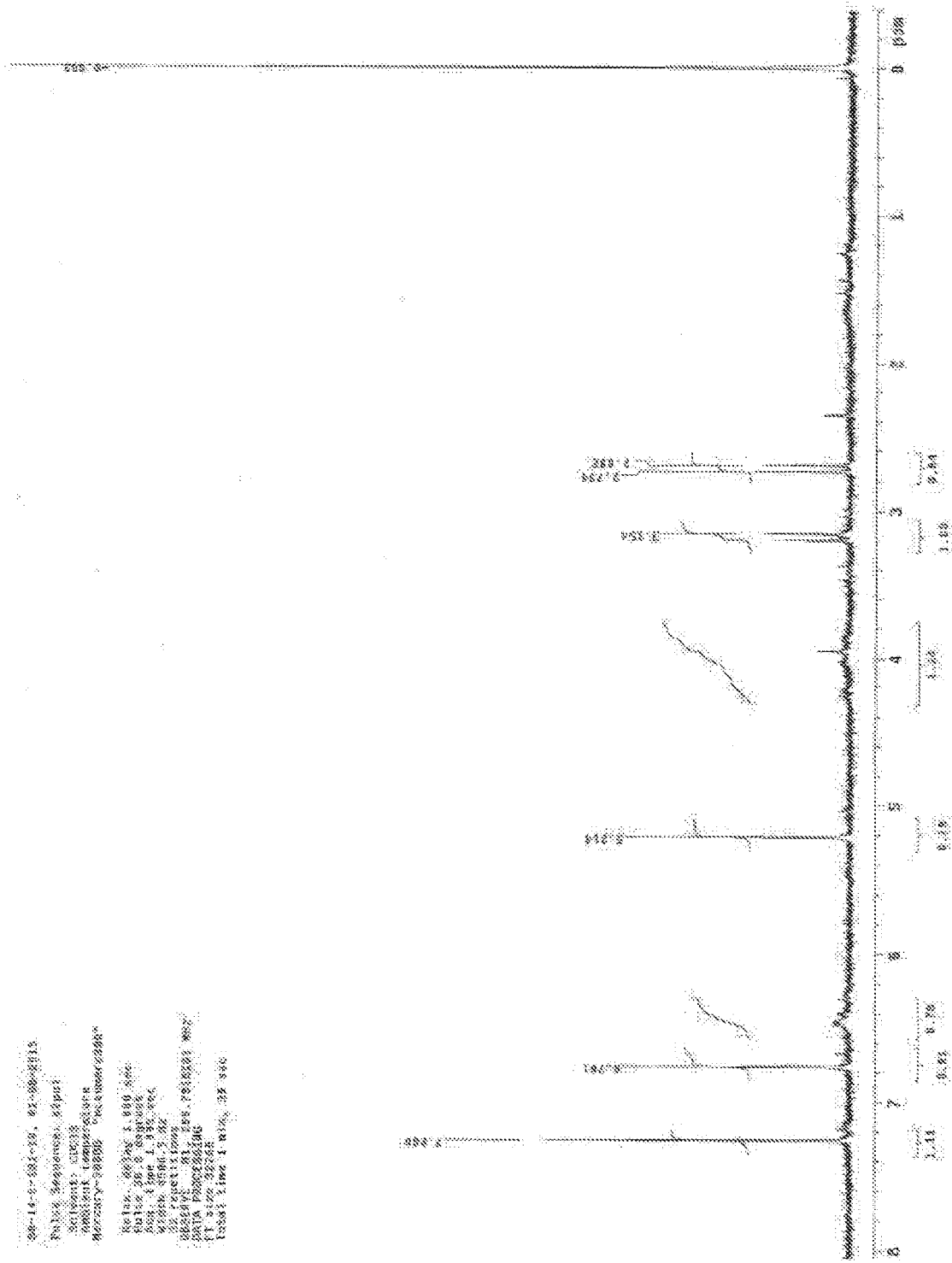
FIG. 2A shows an exemplary $^1$H NMR analysis of reaction product using bis(cyclopentadienyl)zirconium triflate-THF complex in the presence of Me$_3$Al.
Figure 2B:
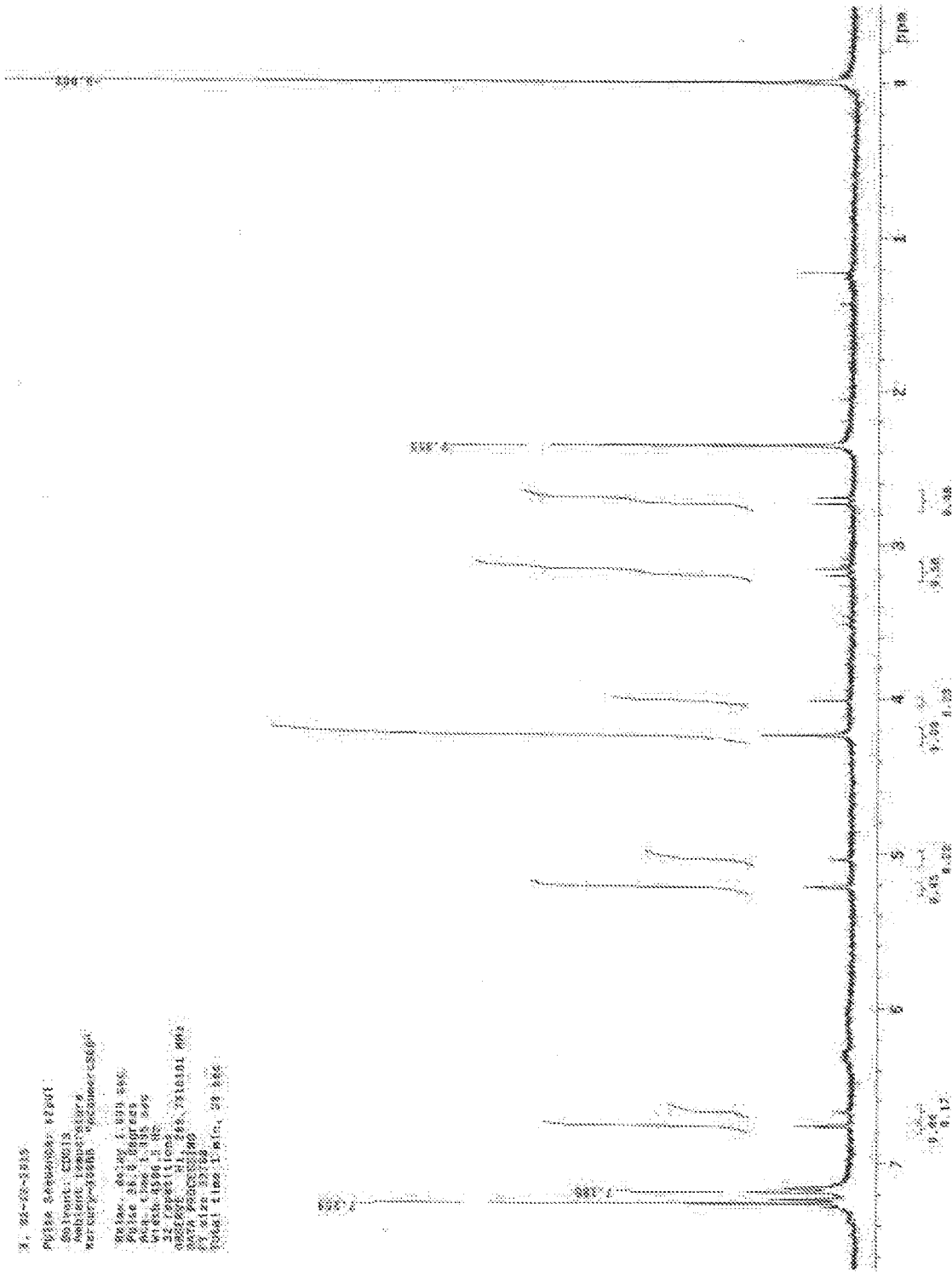
FIG. 2B shows an exemplary $^1$H NMR analysis of reaction product using bis(cyclopentadienyl)zirconium triflate-THF complex in the absence of Me$_3$Al.

Reaction with aluminum chloride showed a product spot without the presence of drying agent trimethyl aluminum (Me$_3$Al). No product was observed in the presence of Me$_3$Al. $^1$H nuclear magnetic resonance (NMR) shows a mixture of desired exo (~5.2 ppm) and undesired endo (~5 ppm) in ~3:1 ratio along with some starting material (SM) present (~4 ppm) (see, e.g., FIG. 1). FIG. 1 shows $^1$H NMR peaks at 7.261 ppm, 7.255 ppm, 7.187 ppm, 4.238 ppm, 2.356 ppm, 1.314 ppm, 1.225 ppm, −0.000 ppm, and −0.002 ppm. Similar results were observed for tin triflate. Both bis(cyclopentadienyl)zirconium triflate-THF complex and bis(cyclopentadienyl)titanium triflate show a cleaner TLC analysis in the presence of Me$_3$Al compared to the absence of Me$_3$Al. $^1$H NMR shows only the desired product. FIG. 2A and FIG. 2B show $^1$H NMR results for bis(cyclopentadienyl)zirconium triflate-THF complex with and without Me$_3$Al, respectively. FIG. 2A shows $^1$H NMR peaks at 7.260 ppm, 6.761 ppm, 5.214 ppm, 3.154 ppm, 2.734 ppm, 2.692 ppm, and −0.003 ppm. FIG. 2B shows $^1$H NMR peaks at 7.255 ppm, 7.186 ppm, 2.355 ppm, and −0.002 ppm. Very little, if any, of the undesired endo isomer formed.

Boron trifluoride-diethyl etherate complex showed some product in the presence of Me$_3$Al. $^1$H NMR shows product along with undesired endo-isomer and starting material.

TMS triflate showed some product in the presence of Me$_3$Al.

Bis(cyclopentadienyl)zirconium triflate-THF complex without the presence of trimethyl aluminum afforded a mixture of two isomers as oppose to single isomer when trimethyl aluminum is used as shown by NMR. This indicates the importance of the presence of trimethyl aluminum in some reactions for the desired stereoselectivity. Apparently all reactions with the absence of trimethyl aluminum afforded a mixture of isomers. The presence of trimethyl aluminum afforded a mixture of isomers for some LA. Single isomer formed for Zr, Ti-triflate and TMS-triflate.

Bis(cyclopentadienyl)zirconium triflate-THF complex is desirable for its stereoselectivity for the desired exo-isomer. Aluminum chloride and boron trifluoride-diethyl etherate complex can be desirable as they can be available at low cost.

Example 10: Two-Step Process of Desulfurization and Hydrogenation

Previous investigation indicated low yield of cantharidin (e.g., 10-12%) during the Raney Ni mediated hydrogenation and desulfurization in one pot. Some yield may be lost to the retro-DA chemistry once the sulfur is gone prior to double bond reduction. A two-step process of double bond reduction using Pd-C and hydrogen followed desulfurization with Raney Ni was investigated:

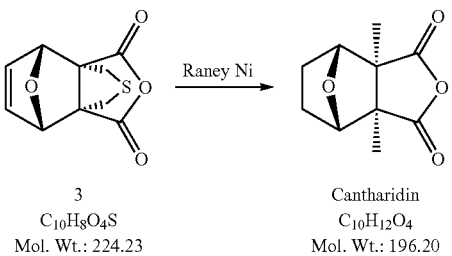
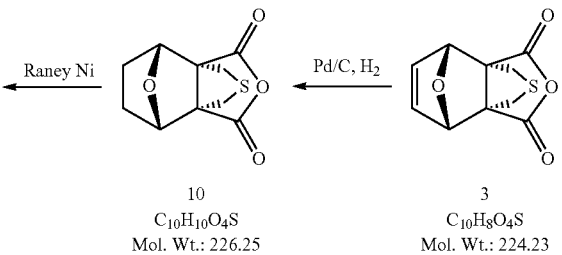

3
C$_{10}$H$_8$O$_4$S
Mol. Wt.: 224.23

Cantharidin
C$_{10}$H$_{12}$O$_4$
Mol. Wt.: 196.20

10
C$_{10}$H$_{10}$O$_4$S
Mol. Wt.: 226.25

3
C$_{10}$H$_8$O$_4$S
Mol. Wt.: 224.23

A Pd-C (10%) hydrogenation of compound 3 (5 g) was performed to afford the double bond reduced material (compound 10) while keeping the sulfur intact. 4.1 g of pure product was isolated (82% yield).

Raney Nickel chemistry was performed on the double bond reduced compound on a 1 g scale in ethyl acetate for 4 hours under 30 psi of hydrogen at 50° C.:

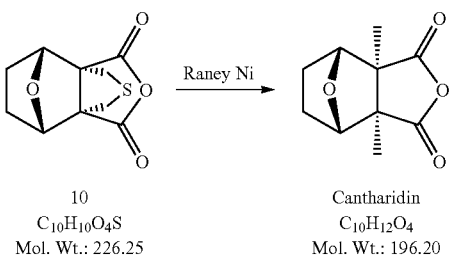

| 10 | Cantharidin |
|---|---|
| C₁₀H₁₀O₄S | C₁₀H₁₂O₄ |
| Mol. Wt.: 226.25 | Mol. Wt.: 196.20 |

Partial conversion was observed by NMR. The reaction was extended for 16 hours at 50 psi of hydrogen at 50° C. The reaction mixture was filtered hot through a pad of celite and washed with hot ethyl acetate (100 mL). The filtrate was concentrated and the solid product was triturated with small amount of ethyl acetate to afford 150-mg (17%) of the product. NMR analysis appears consistent. The filtrate was concentrated to afford 350 mg of a semi-solid. NMR analysis shows some product present. A second reaction was performed at 30 psi of hydrogen at 50° C.; 0.3 g (34%) of the product was isolated after filtration, concentration and titration.

The double bond hydrogenation afforded a better yield than a single step process.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A process comprising:

a) providing a first compound of formula (1):

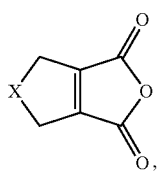

(1)

wherein X is selected from the group consisting of S, O, CH$_2$, CHR$^1$, CR$^1$R$^2$, NH, NR$^1$, and NR$^1$R$^2$, wherein said R$^1$ and R$^2$ are each independently selected from alkyl, aryl, heteroaryl, alkoxy, amine, alcohol, and halogen or together are a carbonyl, alkenyl, imine, or oxime, wherein said R$^1$ and R$^2$ are each optionally independently substituted; and b) forming a second compound having formula (2):

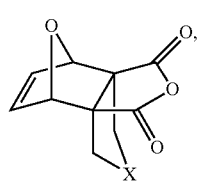

(2)

wherein X is selected from the group consisting of S, O, CH$_2$, CHR$^1$, CR$^1$R$^2$, NH, NR$^1$, and NR$^1$R$^2$, wherein said R$^1$ and R$^2$ are each independently selected from alkyl, aryl, heteroaryl, alkoxy, amine, alcohol, and halogen or together are a carbonyl, alkenyl, imine, or oxime, wherein said R$^1$ and R$^2$ are each optionally independently substituted;

wherein said second compound is formed by reacting said first compound with furan in the presence of at least one Lewis acid selected from the group consisting of bis(cyclopentadienyl)zirconium(IV) bis(trifluoromethanesulfonate)tetrahydrofuran complex, bis(cyclopentadienyl)titanium(IV) bis(trifluoromethanesulfonate), and trimethylsilyl trifluoromethanesulfonate.

2. The process of claim 1, wherein the Lewis acid is bis(cyclopentadienyl)titanium(IV) bis(trifluoromethanesulfonate) or trimethylsilyl trifluoromethanesulfonate.

3. The process of claim 1, wherein the Lewis acid is bis(cyclopentadienyl)zirconium(IV) bis(trifluoromethanesulfonate)tetrahydrofuran complex.

4. The process of claim 1, wherein the reaction is carried out in the presence of Me$_3$Al.

5. The process of claim 1, wherein the compound of formula (1) is of the formula:

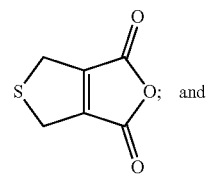

and the compound of formula (2) is of the formula:

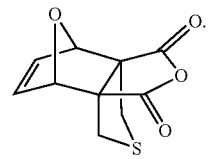 [SMILES: O=C1OC(=O)C23CSCC12C1C=CC3O1]

6. The process of claim 1, wherein the reaction is carried out in a solvent.

7. The process of claim 6, wherein the solvent is selected from the group consisting of acetone, ethyl acetate, isopropyl acetate, benzene, xylenes, toluene, chlorobenzene, methylene chloride, ethylene dichloride, dioxane, THF, tert-butyl methyl ether, diisopropyl ether, 1,2-dimethoxy ethane (glyme), acetonitrile, methanol, and water.

8. The process of claim 1, wherein the reaction is carried out at a temperature ranging from −20° C. to 150° C.

9. The process of claim 8, wherein the reaction is carried out at approximately room temperature.

10. The process of claim 4, wherein the compound of formula (2) is formed in an exo-to-endo product ratio of at least 85:15.

11. The process of claim 4, wherein the compound of formula (2) is formed in an exo-to-endo product ratio of at least 90:10.

12. The process of claim 4, wherein the compound of formula (2) is formed in an exo-to-endo product ratio of at least 95:5.

13. The process of claim 4, wherein the compound of formula (2) is formed in an exo-to-endo product ratio of at least 99:1.

14. The process of claim 1, further comprising a step of hydrogenating the compound of formula (2).

15. The process of claim 5, further comprising a step of hydrogenating the compound of formula (2) to form compound (10):

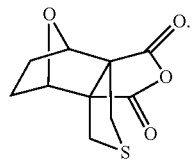

(10)

16. The process of claim 15, wherein the step of hydrogenating is carried out in the presence of Pd/C and hydrogen.

17. The process of claim 15, further comprising a step of desulfurizing compound (10) to form cantharidin:

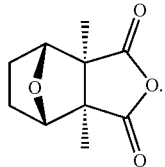

18. The process of claim 17, wherein the step of desulfurizing is carried out in the presence of Raney Nickel, Ni(II)/NaBH$_4$, Co(II)/NaBH$_4$, Li/EtNH$_2$, LAH/TiCl$_3$, LAH/CuCl$_2$, Ni(II)/Zn, Ni(II)/Al, or LAH/Cp$_2$Ni.

19. The process of claim 18, wherein the step of desulfurizing is carried out in the presence of Raney Nickel.

20. The process of claim 2, wherein the reaction is carried out in the presence of Me$_3$Al.

21. The process of claim 3, wherein the reaction is carried out in the presence of Me$_3$Al.

22. The process of claim 5, wherein the Lewis acid is bis(cyclopentadienyl)titanium(IV) bis(trifluoromethanesulfonate) or trimethylsilyl trifluoromethanesulfonate.

23. The process of claim 5, wherein the Lewis acid is bis(cyclopentadienyl)zirconium(IV) bis(trifluoromethanesulfonate)tetrahydrofuran complex.

24. The process of claim 5, wherein the reaction is carried out in the presence of Me$_3$Al.

25. The process of claim 22, wherein the reaction is carried out in the presence of Me$_3$Al.

26. The process of claim 23, wherein the reaction is carried out in the presence of Me$_3$Al.

27. The process of claim 5, wherein the reaction is carried out in a solvent.

28. The process of claim 27, wherein the solvent is selected from the group consisting of acetone, ethyl acetate, isopropyl acetate, benzene, xylenes, toluene, chlorobenzene, methylene chloride, ethylene dichloride, dioxane, THF, tert-butyl methyl ether, diisopropyl ether, 1,2-dimethoxy ethane (glyme), acetonitrile, methanol, and water.

29. The process of claim 5, wherein the reaction is carried out at a temperature ranging from −20° C. to 150° C.

30. The process of claim 29, wherein the reaction is carried out at approximately room temperature.

31. The process of claim 24, wherein the compound of formula (2) is formed in an exo-to-endo product ratio of at least 85:15.

32. The process of claim 24, wherein the compound of formula (2) is formed in an exo-to-endo product ratio of at least 90:10.

33. The process of claim 24, wherein the compound of formula (2) is formed in an exo-to-endo product ratio of at least 95:5.

34. The process of claim 24, wherein the compound of formula (2) is formed in an exo-to-endo product ratio of at least 99:1.

* * * * *